(12) United States Patent
Fierabracci

(10) Patent No.: US 12,410,431 B2
(45) Date of Patent: Sep. 9, 2025

(54) SHORT INTERFERING RNA TARGETING VARIANT C1858T OF GENE PTPN22

(71) Applicant: Ospedale Pediatrico Bambino Gesu', Rome (IT)

(72) Inventor: Alessandra Fierabracci, Rome (IT)

(73) Assignee: Ospedale Pediatrico Bambino Gesu', Rome (IT)

( * ) Notice: Subject to any disclaimer, the term of this patent is extended or adjusted under 35 U.S.C. 154(b) by 1186 days.

(21) Appl. No.: 17/053,816

(22) PCT Filed: May 8, 2019

(86) PCT No.: PCT/IT2019/050095
§ 371 (c)(1),
(2) Date: Nov. 9, 2020

(87) PCT Pub. No.: WO2019/215772
PCT Pub. Date: Nov. 14, 2019

(65) Prior Publication Data
US 2021/0238607 A1    Aug. 5, 2021

(30) Foreign Application Priority Data

May 9, 2018   (CN) .................... 102018000005182

(51) Int. Cl.
| C12N 15/113 | (2010.01) |
| A61K 9/1271 | (2025.01) |
| A61K 47/69 | (2017.01) |
| A61P 3/10 | (2006.01) |

(52) U.S. Cl.
CPC ........ *C12N 15/1137* (2013.01); *A61K 9/1271* (2013.01); *A61K 47/6911* (2017.08); *A61K 47/6913* (2017.08); *A61P 3/10* (2018.01); *C12N 2310/14* (2013.01); *C12N 2310/351* (2013.01); *C12N 2310/3513* (2013.01); *C12N 2320/32* (2013.01)

(58) Field of Classification Search
CPC ............ C12N 15/1137; C12N 2310/14; C12N 2310/351; C12N 2310/3513; C12N 2320/32; C12N 15/113; A61K 9/1271; A61K 47/6911; A61K 47/6913; A61P 3/10
See application file for complete search history.

(56) References Cited

U.S. PATENT DOCUMENTS

2008/0113351 A1* 5/2008 Naito ........................ A61P 5/26
                                                    536/23.1

OTHER PUBLICATIONS

Wang et al., "The autoimmunity-associated gene PTPN22 potentiates toll-like receptor-driven, type 1 interferon-dependent immunity", Immunity 2013; 39(1):111-22. (Year: 2013).*

Perri et al., "Use of short interfering RNA delivered by cationic liposomes to enable efficient down-regulation of PTPN22 gene in human T lymphocytes", PLoS One, Apr. 24, 2017, 12(4):e0175784. (Year: 2017).*
International Search Report and the Written Opinion Dated Jul. 9, 2019 From the International Searching Authority Re. Application No. PCT/IT2019/050095. (13 Pages).
Rapporto di Ricerca e Opinione Scritta [Search Report and Written Opinion] Dated Sep. 19, 2018 From the Ministero di Sviluppo Economico, Direzionale Generale Sviluppo Produttivo e Competitivita, Ufficio Italiano Brevetti e Marchi Re. Application No. IT201800005182. (7 Pages).
Naito et al. "WO 2005/116204-A/193647: Double Strand Polynucleotides Generating RNA Interference", Database EMBL [Online], XP002784061, Retrieved From EBI Accession No. EM_PAT:FW787121, Database Accession No. FW787121, Apr. 18, 2011.
Perri et al. "Use of Short Interfering RNA Delivered by Cationic Liposomes to Enable Efficient Down-Regulation of PTPN22 Gene in Human T Lymphocytes", Plos One, XP055501498, 12(4): e0175784-1-e0175784-32, Apr. 24, 2017.
Aleandri et al. "How Stereochemistry Affects the Physicochemical Features of Gemini Surfactant Based Cationic Liposomes", Soft Matter, 8(21): 5904-5915, Published Online Apr. 24, 2021.
Andersen et al. "Complex Multi-Block Analysis Identifies New Immunologic and Genetic Disease Progression Patterns Associated With the Residual Beta-Cell Function 1 Year After Diagnosis of Type 1 Diabetes", Plos One, 8(6): e64632-1-e64632-8, Jun. 5, 2013.
Andreakos et al. "Amphoteric Liposomes Enable Systemic Antigen-Presenting Cell-Directed Delivery of CD40 Antisense and Are Therapeutically Effective in Experimental Arthritis", Arthritis & Rheumatism, 60(4): 994-1005, Apr. 2009.
Atkinson "Type 1 Diabetes", The Lancet, 383(9911): 69-82, Jan. 4, 2014.
Bello et al. "Role of the Spacer Stereochemistry on the Aggregation Properties of Cationic Gemini Surfactants", Langmuir, 22(22): 9333-9338, Oct. 24, 2006.
Blasetti et al. "Role of the C1858T Polymorphism of Protein Tyrosine Phosphatase Non-Receptor Type 22 (PTPN22): in Children and Adolscents With Type 1 Diabetes", The Pharmacogenomics Journal, 17(2): 186-191, Published Online Feb. 3, 2016.
Bombelli et al. "Efficiency of Liposomes in the Delivery of a Photosensitizer Controlled by the Stereochemistry of A Gemini Surfactant Component", Molecular Pharmaceutics, 7(1): 130-137, Published on Web Nov. 24, 2009.
Bombelli et al. "Efficient Transfection of DNA by Liposomes Formulated With Cationic Gemini Amphiphiles", Journal of Medicinal Chemistry, 48(16): 5378-5382, Aug. 11, 2005.
Bombelli et al. "Role of the Spacer of Cationic Gemini Amphiphiles in the Condensation of DNA", Langmuir, 21(23): 10271-10274, Nov. 8, 2005.

(Continued)

*Primary Examiner* — Abigail Vanhorn
*Assistant Examiner* — Stephanie L Sullivan

(57) ABSTRACT

The present invention concerns a short Interfering RNA, which is variant C1858T PTPN22 short interfering RNA duplexes (siRNA), and uses thereof in medical field in the prevention and treatment of autoimmune diseases.

11 Claims, 15 Drawing Sheets
Specification includes a Sequence Listing.

(56) References Cited

OTHER PUBLICATIONS

Bottini et al. "A Functional Variant of Lymphoid Tyrosine Phospahtase Is Associated With Type I Diabetes", Nature Genetics, 36(4): 337-338, Published Online Mar. 7, 2004.
Buell et al. "Sialic Acid Mimetics to Target the Sialic Acid-Siglec Axis", Trends in Biochemical Sciences, 41(6): 519-531, Published Online Apr. 13, 2016.
Chelala et al. "PTPN22 R620W Functional Variant in Type 1 Diabetes and Autoimmunity Related Traits", Diebetes, 56(2): 522-526, Feb. 2007.
Dutta et al. "Inhibition of Glycolate Oxidase With Dicer-Substrate SiRNA Reduces Calcium Oxalate in A Mouse Model of Primary Hyperoxaluria Type 1", Molecular Therapy, 24(4): 770-778, Published Online Jan. 13, 2016.
Fierabracci et al. "The Putative Role of Endoplasmic Reticulum Aminoppeptidases in Autoimmunity: Insights From Genomic-Wide Association Studies", Autoimmunity Reviews, 12(2): 281-288, Available Online May 7, 2012.
Gianchecchi et al. "Altered B Cell Homeostasis and Toll-Like Receptor 9-Driven Response in Typw 1 Diabetes Carriers of the C1858T PTPN22 Allelic Variant: Implications in the Disease Pathogenesis", PLoS One, 9(10): e110755-1-e110755-10, Oct. 21, 2014.
Gianchecchi et al. "The Putative Role of the C1858T Polymorphism of Protein Tyrosine Phosphatase PTPN22 Gene in Autoimmunity", Autoimmunity Reviews, 12(7): 717-725, Available Online Dec. 20, 2012.
Gourh et al. "Association of the PTPN22 R620W Polymorphism With Anti-Topoisomerase I- and Anticentromere Antibody-Positive Systemic Sclerosis", Arthritis & Rheumatism, 54(12): 3945-3953, Dec. 2006.
Harron et al. "Incidence Rate Trends in Childhood Type 1 Diabetes in Yorkshire, UK 1978-2007: Effects of Deprivation and Age at Diagnosis in the South Asian and Non-South Asian Population", Diabetic Medicine, 28(12): 1508-1513, Dec. 2011.
He et al. "A Potent and Selective Small-Molecule Inhibitor for the Lymphoid-Specific Tyrosine Phosphatase (Lyp), A Target Associated With Autoimmune Diseases", Journal of Medicinal Chemistry, 56(12): 4990-5008, Published Online Jun. 6, 2013.
Hermann et al. "Lymphoid Tyrosine Phosphatase (LYP/PTPN22) Arg620Trp Variant Regulates Insulin Autoimmunity and Progression to Type 1 Diabetes", Diabetologia,49(6): 1198-1208, Published Online Apr. 14, 2006.
Hinks et al. "Association Between the PTPN22 Gene and Rheumatoid Arthritis and Juvenile Idiopathic Arthritis in a UK Population: Further Support That PTPN22 Is an Autoimmunity Gene", Arthritis & Rheumatism, 52(6): 1694-1699, Jun. 2005.
Hughes et al. "Autoimmune Diseases in Children and Adults With Type 1 Diabetes From the TID Exchange Clinic Registry", The Journal of Clinical Endocrinology and Metabolism, 101(12): 4931-4937, Published Online Sep. 27, 2016.
Jagiello et al. "The PTPN22 620W Allele Is a Risk Factor for Wegener's Granulomatosis", Arthritis & Rheumatism, 52(12): 4039-4043, Dec. 2005.
Joly et al. "Decreased Hypersensitivity Reactions With Carboplatin-Pegylated Liposomal Doxorubicin Compared to Carboplatin-Paclitaxel Combination: Analysis From the GCIG CALIPSO Relapsing Ovarian Cancer Trial", Gynecology Oncology, 122(2): 226-232, Available Online May 14, 2011.
Kudoh et al. "Effects of Bevacizumab and Pegylated Liposomal Doxorubicin for the Patients With recurrent or Refractory Ovarian Cancers", Gynecologic Oncology, 122(2): 233-237, Available Online May 23, 2011.
Lee et al. "Genetic Risk Factors for Rheumatoid Arthritis Differ in Caucasian and Korean Populations", Arthritis & Rheumatism, 60(2): 364-371, Feb. 2009.
Li et al. "The Common, Autoimmunity-Predisposing 620Arg> Trp Variant of PTPN22 Modulates Macrophage Function and Morphology", Journal of Autoimmunity, 79: 74-83, Published Online Feb. 22, 2017.
Lin et al. "CRISPR-Cas9 Mediated Modification of the NOD Mouse Genome With PTPN22[R619W] Mutation Increases Autoimmune Diabetes", Diabetes, 65(8): 2134-2138, Published Online Apr. 26, 2016.
Liu "Targeting Polo-Like Kinase: A Promising Therapeutic Approach for Cancer Treatment", Translational Oncology, 8(3): 185-195, Jun. 2015.
Mainardi-Novo et al. "The PTPN22 1858T Allele But Not Variants in the Proximal Promoter Region of IL-21 Gene Is Associated With the Susceptibility to Type 1 Diabetes and the Presence of Autoantibodies in A Brazilian Cohort", Clinical and Experimental Immunology, 172(1): 16-22, Apr. 2013.
Maine et al. "PTPN22 Alters the Development of Regulatory T Cells in the Thymus", The Journal of Immunology, 188(11): 5267-5275, Published Online Apr. 25, 2012.
Maziarz et al. "The Association Between the PTPN22 1858C> T Variant and Type 1 Diabetes Depends on HLA Risk and GAD65 Autoantibodies", Genes and Immunity, 11(5): 406-415, Published Online May 6, 2010.
McLachlan et al. "Breaking Tolerance to Thyroid Antigens: Changing Concepts in Thyroid Autoimmunity", Endocrine Reviews, 35(1): 59-105, Published Online Oct. 3, 2013.
Metzler et al. "The Autoimmune Risk Variant PTPN22 C1858T Alters B Cell Tolerance at Discrete Checkpoints and Differentially Shapes the Naive Repertoire", The Journal of Immunology, 199(7): 2249-2260, Published Online Aug. 11, 2017.
Nielsen et al. "Sex-Specific Association of the Human PTPN22 1858T-Allele With Type 1 Diabetes", International Journal of Immunogenetics, 34(6): 469-473, Dec. 2007.
Nielsen et al. "The PTPN22 C1858T Gene Variant Is Associated With Proinsulin in New-Onset Type 1 Diabetes", BMC Medical Genetics, 12(1): 41-1-41-6, Mar. 23, 2011.
Opanasopit et al. "Type and Composition of Surfactants Mediating Gene Transfection of Polyethylenimine-Coated Liposomes", International Journal of Nanomedicine, 6: 975-983, Published Online May 9, 2011.
Orozco et al. "Association of a Functional Single-Nucleotide Polymorphism of PTPN22, Encoding Lymphoid Protein Phosphatase, With Rheumatoid Arthritis and Systemic Lupus Erythematosus", Arthritis & Rheumatism, 52(1): 219-224, Jan. 2005.
Petre et al. "Liposomal Daunorubicin as Treatment for Kaposi's Sarcoma", International Journal of Nanomedicine, 2(3): 277-288, Sep. 2007.
Petrone et al. "The Protein Tyrosine Phosphatase Nonreceptor 22 (PTPN22) Is Associated With High GAD Antibody Titer in Latent Autoimmune Diabetes in Adults", Diabetes Care, 31(3): 534-538, Published Online Dec. 4, 2007.
Petrone et al. "The PTPN22 1858T Gene Variant in Type 1 Diabetes Is Associated With Reduced Residual Beta-Cell Function and Worse Metabolic Control", Diabetes Care, 31(6): 1214-1218, Jun. 2008.
Rillahan et al. "Click and Pick: Identification of Sialoside Analogues for Siglec-Based Cell Targeting", Angewandte Chemie, 124(44): 11176-11180, Published Online Oct. 4, 2012.
Sadovnick "Genetic Background of Multiple Sclerosis", Autoimmunity Reviews, 11(3): 163-166, Available Online May 18, 2011.
Schoelin et al. "Islet Antibodies and Remaining Beta-Cell Fucntion 8 Years After Diagnosis of Diabetes in Young Adults: A Prospective Follow-Up of the Nationwide Diabetes Incidence Study in Sweden", Journal of Internal Medicine, 255(3): 384-391, Mar. 2004.
Seebach "Herstellung von Hilfsstoffen für die Asymmetrische Syn these aus Weinsäure. Additione von Butyl-Li an Aldehyde in Chiralem Medium", Chemischer Informationsdienst, 8(31): 18-19, # 073, Aug. 2, 1977.
Stanford et al. "Discovery of a Novel Series of Inhibitors of Lymphoid Tyrosine Phosphatase With Activity in Human T Cells", Journal of Medicinal Chemistry, 54(6): 1640-1654, Published Online Feb. 22, 2011.
Vandiedonck et al. "Association of the PTPN22*R620W Polymorphism With Autoimmune Myasthenia Gravis", Annals of Neurology, 59(2): 404-407, Published Online Jan. 23, 2006.
Vang et al. "Autoimmune-Associated Lymphoid Tyrosine Phosphatase Is a Gain-of-Function Variant", Nature Genetics, 37(12): 1317-1319, Published Online Nov. 6, 2005.

(56) References Cited

OTHER PUBLICATIONS

Vang et al. "Inhibition of Lymphoid Tyrosine Phosphatase by Bensofuran Salicyclic Acids", Journal of Medicinal Chemistry, 54(2): 562-571, Published on Web Dec. 29, 2010.
Watts et al. "Silencing Disease Genes in the Laboratory and the Clinic", Journal of Pathology, 226(2): 365-379, Published Online Nov. 9, 2011.
Wiebolt et al. "Endocrine Autoimmune Disease: Genetics Become Complex", European Journal of Clinical Investigation, 40(12): 1144-1155, Published Online Aug. 16, 2010.
Woittiez et al. "Impact of Disease Heterogeneity on Treatment Efficacy of Immunotherapy in Type 1 Diabetes: Different Shades of Gray", Immunotherapy, 7(2): 163-174, Published Online Feb. 25, 2015.
Wu et al. "Autoimmunity-Associated LYP-W620 Does Not Impair Thymic Negative Selection of Autoreactive T Cells", Plos One, 9(2): e86677-1-e86677-14, Feb. 3, 2014.
Zheng et al. "PTPN22 Silencing in the NOD Model Indicates the Type 1 Diabetes-Associated Allele Is Not a Loss-of-Function Variant", Diabetes, 62(3): 896-904, Published Online Nov. 28, 2012.

\* cited by examiner

SEQUENCE LISTING

<160> NUMBER OF SEQ ID NOS: 26

<210> SEQ ID NO 1
<211> LENGTH: 19
<212> TYPE: RNA
<213> ORGANISM: Artificial Sequence
<220> FEATURE:
<223> OTHER INFORMATION: sense siRNA sequence targeting PTPN22 C1858T
      single nucleotide polymorphism

<400> SEQUENCE: 1
guauggacac cugaaucau                                                    19

```
<210> SEQ ID NO 2
<211> LENGTH: 19
<212> TYPE: RNA
<213> ORGANISM: Artificial Sequence
<220> FEATURE:
<223> OTHER INFORMATION: antisense siRNA sequence targeting PTPN22
      C1858T single nucleotide polymorphism

<400> SEQUENCE: 2
augauucagg uguccauac                                                      19

<210> SEQ ID NO 3
<211> LENGTH: 19
<212> TYPE: RNA
<213> ORGANISM: Artificial Sequence
<220> FEATURE:
<223> OTHER INFORMATION: Sense siRNA sequence targeting PTPN22 C1858T
      single nucleotide polymorphism

<400> SEQUENCE: 3
cuuccuguau ggacaccug                                                      19

<210> SEQ ID NO 4
<211> LENGTH: 19
<212> TYPE: RNA
<213> ORGANISM: Artificial Sequence
<220> FEATURE:
<223> OTHER INFORMATION: Antisense siRNA sequence targeting PTPN22
      C1858T single nucleotide polymorphism

<400> SEQUENCE: 4
caggugucca uacaggaag                                                      19

<210> SEQ ID NO 5
<211> LENGTH: 19
<212> TYPE: RNA
<213> ORGANISM: Artificial Sequence
<220> FEATURE:
<223> OTHER INFORMATION: Sense siRNA sequence targeting PTPN22 C1858T
      single nucleotide polymorphism

<400> SEQUENCE: 5
auggacaccu gaaucauuu                                                      19

<210> SEQ ID NO 6
<211> LENGTH: 19
<212> TYPE: RNA
<213> ORGANISM: Artificial Sequence
<220> FEATURE:
<223> OTHER INFORMATION: Antisense siRNA sequence targeting PTPN22
      C1858T single nucleotide polymorphism

<400> SEQUENCE: 6
aaaugauuca gguguccau                                                      19

<210> SEQ ID NO 7
<211> LENGTH: 19
<212> TYPE: RNA
<213> ORGANISM: Artificial Sequence
<220> FEATURE:
<223> OTHER INFORMATION: Sense siRNA sequence targeting PTPN22 C1858T
      single nucleotide polymorphism

<400> SEQUENCE: 7
uguauggaca ccugaauca                                                      19
```

```
<210> SEQ ID NO 8
<211> LENGTH: 19
<212> TYPE: RNA
<213> ORGANISM: Artificial Sequence
<220> FEATURE:
<223> OTHER INFORMATION: Antisense siRNA sequence targeting PTPN22
      C1858T single nucleotide polymorphism

<400> SEQUENCE: 8
ugauucaggu guccauaca                                                        19

<210> SEQ ID NO 9
<211> LENGTH: 19
<212> TYPE: RNA
<213> ORGANISM: Artificial Sequence
<220> FEATURE:
<223> OTHER INFORMATION: Sense siRNA sequence targeting PTPN22 C1858T
      single nucleotide polymorphism

<400> SEQUENCE: 9
uauggacacc ugaaucauu                                                        19

<210> SEQ ID NO 10
<211> LENGTH: 19
<212> TYPE: RNA
<213> ORGANISM: Artificial Sequence
<220> FEATURE:
<223> OTHER INFORMATION: Antisense siRNA sequence targeting PTPN22
      C1858T single nucleotide polymorphism

<400> SEQUENCE: 10
aaugauucag guguccaua                                                        19

<210> SEQ ID NO 11
<211> LENGTH: 19
<212> TYPE: DNA
<213> ORGANISM: Homo sapiens

<400> SEQUENCE: 11
gtatggacac ctgaatcat                                                        19

<210> SEQ ID NO 12
<211> LENGTH: 19
<212> TYPE: DNA
<213> ORGANISM: Homo sapiens

<400> SEQUENCE: 12
atgattcagg tgtccatac                                                        19

<210> SEQ ID NO 13
<211> LENGTH: 19
<212> TYPE: DNA
<213> ORGANISM: Homo sapiens

<400> SEQUENCE: 13
cttcctgtat ggacacctg                                                        19

<210> SEQ ID NO 14
<211> LENGTH: 19
<212> TYPE: DNA
<213> ORGANISM: Homo sapiens

<400> SEQUENCE: 14
caggtgtcca tacaggaag                                                        19
```

```
<210> SEQ ID NO 15
<211> LENGTH: 19
<212> TYPE: DNA
<213> ORGANISM: Homo sapiens

<400> SEQUENCE: 15
atggacacct gaatcattt                                              19

<210> SEQ ID NO 16
<211> LENGTH: 19
<212> TYPE: DNA
<213> ORGANISM: Homo sapiens

<400> SEQUENCE: 16
aaatgattca ggtgtccat                                              19

<210> SEQ ID NO 17
<211> LENGTH: 19
<212> TYPE: DNA
<213> ORGANISM: Homo sapiens

<400> SEQUENCE: 17
tgtatggaca cctgaatca                                              19

<210> SEQ ID NO 18
<211> LENGTH: 19
<212> TYPE: DNA
<213> ORGANISM: Homo sapiens

<400> SEQUENCE: 18
tgattcaggt gtccataca                                              19

<210> SEQ ID NO 19
<211> LENGTH: 19
<212> TYPE: DNA
<213> ORGANISM: Homo sapiens

<400> SEQUENCE: 19
tatggacacc tgaatcatt                                              19

<210> SEQ ID NO 20
<211> LENGTH: 19
<212> TYPE: DNA
<213> ORGANISM: Homo sapiens

<400> SEQUENCE: 20
aatgattcag gtgtccata                                              19

<210> SEQ ID NO 21
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 21
cgaccacttt gtcaagctca                                             20

<210> SEQ ID NO 22
<211> LENGTH: 20
<212> TYPE: DNA
<213> ORGANISM: Artificial Sequence
<220> FEATURE:
<223> OTHER INFORMATION: GAPDH reverse primer
```

```
<400> SEQUENCE: 22
aggggtctac atggcaactg                                               20

<210> SEQ ID NO 23
<211> LENGTH: 20
<212> TYPE: DNA
<213> ORGANISM: Artificial Sequence
<220> FEATURE:
<223> OTHER INFORMATION: PTPN22 forward primer

<400> SEQUENCE: 23
gctgtactag caactgctcc                                               20

<210> SEQ ID NO 24
<211> LENGTH: 20
<212> TYPE: DNA
<213> ORGANISM: Artificial Sequence
<220> FEATURE:
<223> OTHER INFORMATION: PTPN22 reverse primer

<400> SEQUENCE: 24
ccagcttcct caaccacaat                                               20

<210> SEQ ID NO 25
<211> LENGTH: 17
<212> TYPE: DNA
<213> ORGANISM: Artificial Sequence
<220> FEATURE:
<223> OTHER INFORMATION: PTPN22 T1858 forward primer

<400> SEQUENCE: 25
cagctgtact agcaact                                                  17

<210> SEQ ID NO 26
<211> LENGTH: 17
<212> TYPE: DNA
<213> ORGANISM: Artificial Sequence
<220> FEATURE:
<223> OTHER INFORMATION: PTPN22 T1858

<400> SEQUENCE: 26
aggtgtccat acaggaa                                                  17
```

SHORT INTERFERING RNA TARGETING VARIANT C1858T OF GENE PTPN22

RELATED APPLICATIONS

This application is a National Phase of PCT Patent Application No. PCT/IT2019/050095 having International filing date of May 8, 2019, which claims the benefit of priority of Italian Patent Application No. 102018000005182 filed on May 9, 2018. The contents of the above applications are all incorporated by reference as if fully set forth herein in their entirety.

SEQUENCE LISTING STATEMENT

The ASCII file, entitled 85357SequenceListing.txt, created on Nov. 9, 2020, comprising 5,480 bytes, submitted concurrently with the filing of this application is incorporated herein by reference. The sequence listing submitted herewith is identical to the sequence listing forming part of the international application.

FIELD AND BACKGROUND OF THE APPLICATION

The present invention concerns a short interfering RNA targeting variant C1858T of gene PTPN22. In particular, the present invention concerns a short Interfering RNA, which is variant C1858T PTPN22 short interfering RNA duplexes (siRNA), and uses thereof in medical field in the prevention and treatment of autoimmune diseases.

Autoimmune diseases are a heterogeneous group of disorders affecting various organs or systems, whose incidence is increasing worldwide. They arise from a complex interplay of (poly) genetic and environmental factors greatly influenced by post-translational and post-transcriptional events and somatic mutations. With the advent of genome-wide linkage, candidate gene association studies and genome-wide association studies, in addition to HLA, several single nucleotide polymorphisms (SNPs) were discovered to underlie the pathogenesis of autoimmunity [reviewed (rev) in Gianchecchi E, Palombi M Fierabracci A, Autoimmun Rev 2013; 12, 717-25]. Experimental studies demonstrate that autoimmunity derives from the escape of antigen-specific autoreactive T cells in the periphery from the thymus in the perinatal age. This is caused by a failure in promiscuous thymic expression of peripheral organ-specific antigens in the same organ. Among the cellular players, T helper (Th) cells, that escaped mechanisms of self-tolerance, initiate inflammation and provide help to autoreactive B cells mediated by proinflammatory cytokines. The activation, expansion and subsequent differentiation of mature B cells in plasma cells producing autoantibodies further contribute to tissue damage. Th cells, when encountering the self- or cross-reactive antigen, activate, expand and differentiate into Th1, Th2 subtypes, regulatory T (Treg) and Tr1 cells. Th1 and Th2 cells secrete two different and mutually inhibitory pathways of cytokines. Th1 cells secrete interleukin 2 (IL-2) and interferon gamma (IFN-γ), while Th2 cells secrete interleukin 4 (IL-4), interleukin 5 (IL-5) and interleukin 10 (IL-10).

It is known that insulin-dependent diabetes mellitus (Type 1 diabetes, T1D) (Atkinson 2014) and autoimmune thyroid disease (ATD), including Graves' disease and Hashimoto's thyroiditis (HT) (Mclachlan 2014) are organ-specific T cell mediated diseases, with T cell infiltration resulting in dysfunction of the target organ, i.e. the pancreatic islet in T1D and the thyroid in ATD. The disease combination is known as autoimmune polyglandular syndrome Type 3 variant (APS3v) (Hughes 2016). In addition to the presence of islet-cell antibodies (Abs) (ICA), or Abs to glutamic acid decarboxylase (GADA), to second islet antigen (IA-2 Abs) and to insulin (IAA), up to 20% of T1D patients have circulating thyroid Abs (ATA) with 50% of these progressing to clinical ATD. T1D is the third most common metabolic disorder in the world after obesity and thyroid disorders. Recent epidemiological studies estimate that the incidence of autoimmunity and, in particular of T1D, has increased over the past 30-40 years worldwide in children <15 years (0.1/100.000 in China and 40.9/100.000 in Finland); the average annual increase is 2.8% worldwide and 3.2% in Europe (Harron 2011). Clinically, T1D presents with interrelated metabolic, vascular and neuropathic sequelae and, since the disease onset, if it is not promptly treated with insulin, severe clinical manifestations can occur such as ketoacidosis, potential coma and death. In HT, L-T4 treatment is also administered to avoid the additional metabolic symptoms of hypothyroidism that could lead to cardiac dysfunction, myxedematous coma and, especially in infancy, growth retard and mental retardation. If the only current treatment of autoimmune endocrine disorders is the substitutive administration of the deficient hormone, especially in case of T1D, insulin treatment administered in multiple daily injections will never reproduce the physiological circadian rhythm of the molecule. The treatment always rescues the patient from a certain death but does not cure the autoimmune disease. A significant advance beyond the state of art is therefore the effect that any immunotherapeutic intervention may play in halting the pathogenic immunological mechanisms, therefore preserving the residual hormone producing cells. This could produce a significant improvement on the treatment. In particular, regarding insulin treatment, the associated immunotherapeutic strategy may help to improve the stability of the metabolic course of the disease avoiding the typical 'instability' requiring adjustments on daily insulin administration and continuous glucose monitoring, thereby preventing or reducing long-term complications.

Several immunotherapeutic approaches have being experimented in T1D. However, most of the trials either using antigen-specific therapies, T and B lymphocytes targets, anti-inflammatory approaches, cytokines or stem cells failed to achieve insulin-independence in T1D patients. Furthermore whenever the results of Phase I and Phase II trials were promising, large randomized controlled trials did not reach primary endpoints (Woittiez 2015). The reason may be related to the contribution of environmental factors, dosing, time/duration of treatment but also disease heterogeneity since several gene variations are present in both ATD and T1D ((Wiebolt 2010) and could influence their etiopathogenesis. As regards several immunogenetic investigations on T1D susceptibility have established a relevant role of major histocompatibility complex (MHC) as well as non-MHC genes, among the others the latter include INS-VNTR, CTLA-4, SUMO-4 and PTPN22 (Bottini 2004, rev in Gianchecchi 2013).

SUMMARY OF THE INVENTION

In the light of the above, it is therefore apparent the need to provide new therapeutic methods and compounds for the treatment of autoimmune diseases, which are able to overcome the disadvantages of the known therapies.

As regards, it is known that the PTPN22 (protein tyrosine phosphatase N22 gene) C1858T mutation, which changes amino acid residue 620 from Arg (R) to Trp (W) (R620W) in the lymphoid tyrosine phosphatase Lyp protein (rev in Gianchecchi 2013, Perri 2017), plays a potential pathophysiological role.

R620W is strongly associated with T1D in humans increasing the risk of disease by 2-4 fold (rev in Perri 2017). It is also known that, in addition to T1D and APS3v, the PTPN22 variant was also found associated with neurological disorders such as myasthenia gravis (Vandiedonck 2006) and multiple sclerosis (Sadovnick 2012). Furthermore, regarding non-organ specific autoimmune conditions, the same polymorphism was found associated with systemic lupus erythematosus (SLE) (Orozco 2005), Wegener's granulomatosis (Jagiello 2005) and rheumatoid arthritis (RA) (Hinks 2005) in the Caucasian population. In particular regarding RA, the association with PTPN22 gene variant was the strongest among non-HLA genes, second only to MHC. The correlation between R620W variant and the onset of RA (Lee 2009) and T1D is not reported in Asian populations. The allele was also found in association with systemic sclerosis, especially in anti-topoisomerase 1 (Topo1) and anti-centromere antibody (ACA)-positive patients (rev. in Gourh 2006).

In unravelling mechanistic insights, Lyp is a negative regulator of T cell antigen receptor (TCR) signaling by acting in interplay with C-terminal Src kinase (CSK). The effect of the variant Lyp is still debated in literature. Most studies support a 'gain of function' model since the variant phosphatase causes a more potent regulation of T cell activation (Vang 2005) with paradoxical reduced T cell activation. Peripheral T lymphocytes of T1D patients are indeed hyporesponsive to in vitro stimulation with monoclonal antibodies (mAbs) to CD3 (anti-CD3) (Vang 2005). Lyp variant could produce subtle TCR signaling defects and affect the establishment of immunological tolerance at the thymus level in perinatal age and escape of autoreactive T lymphocytes, through positive selection of otherwise negatively selected autoimmune T cells. Altered B cell homeostasis and Toll-Like receptor (TLR) 9-driven response in T1D carriers of the PTPN22 C1858T allelic variant were also observed (rev. in (Gianchecchi 2013, Gianchecchi 2014), confirming its influence on both innate and adaptive immune responses. Further, animal models provide evidence that the variant alters B cell tolerance augmenting BCR (B cell receptor) and coreceptor programs through B cell development (Metzel 2017). In mice 620Arg>Trp macrophages are more active in T cell stimulation with enhanced phagocytosis, higher expression of MHC class II (MHCII) antigen-presenting molecules and B7 coactivation ligands (Li 2017). Recent studies highlighted the variant effect on regulatory T cells (Tregs). As regards Maine et al (2012) (Maine 2012) demonstrated in knockout mice alterations of the peripheral Tregs while increasing their thymic selection. Other studies (Wu 2014, Zheng 2013) also report a 'gain of function' model of Treg selection although PTPN22 knockout indeed caused reduced TCR signaling. Overall, possible effects on T cell subgroups other than Treg or additional effects on the immune system have to be also considered (Sharp 2015). Further, in the 'gain of function' model, an increase in T cell activity may occur through loss of self-tolerance of peripheral T cells. The 'loss of function' model implies that a Lyp degradation is associated with lymphocyte and dendritic cell hyper responsiveness (rev in Perri 2017). In the last model, putatively the loss of self-tolerance occurs earlier in the T cell life to be subsequently activated by auto antigens (Sharp 2015). Whichever model is adopted in supporting the pathogenic effect of the variant this remains a valid target for 'tailored' treatment throughout its down-modulation/knockdown in T1D and APS3v patients since it would anyway restore the net effect of the normal allele.

It is known that although some Type 1 diabetic subjects loose β cell function completely soon after diagnosis, others retain partial function in the long-term disease (Scholin 2004). This suggests that in T1D, the natural course of beta cell destruction may vary considerably; however, genetic variability may influence disease characteristics and course of disease. Metanalysis investigations come in support of the fact that in the Caucasian 20 population PTPN22 variant is a remarkable risk factor for T1D with males being more susceptible to disease than females. Furthermore, the variant is significantly associated with T1D even in a population at reduced prevalence. The variant not only confers predisposition for T1D especially in European and American populations but it can also represents a prognostic factor. The impact of the C1858T PTPN22 mutation in disease variability has been evaluated by unravelling its association with age of onset, autoantibodies levels, B cell residual function and metabolic control in patients.

Andersen et al (2013) emphasizes a correlation between the presence of the variant with an earlier disease onset, or a more rapid decline of the beta cell reservoir upon the initial autoimmune attack. Especially in female patients C1858T variant was associated with an earlier disease onset (Nielsen 2007) and an increased frequency of GADA and Tg Abs (Mainardi-Novo 2013). As regards increased GADA levels were found in patients with longer disease duration (Petrone 2008) or long-term persistence of GADA (Chelala 2007) or with GAD positivity in T1D patients (Maziarz 2010). Further studies suggest that the variant can influence the progression from preclinical to clinical diabetes in individuals with circulating islet cell autoantibodies (Hermann 2006). Additionally, the variant allele correlated with worse metabolic control in long-term diabetes (Petrone 2008). Fasting c-peptide levels and HbA1C levels were significantly higher in carriers of the variant than in homozygotes for C1858 from diagnosis through 12 months of intensive insulin therapy, independently of age of onset, sex and HLA risk groups. The trend in c-peptide and HbA1C levels in the 12 months period did not differ significantly between carriers and non-carriers of the variant and insulin dose was similar. This led to hypothesize that carriers of the variant experienced a more destructive beta cell damage and maintained significant lower levels of c-peptide compared to C1858 homozygotes within the first year. In the study by Nielsen et al (2011) higher proinsulin levels over 12 months were also reported with no effect on stimulated c-peptide levels while higher proinsulin/c-peptide ratio and no difference in the insulin-dose adjusted HbA1c. However, the variant could affect the interplay of autoimmunity mechanisms and the development of compensatory metabolic responses over time (Blasetti 2017).

In the light of the foregoing Lyp selective high affinity noncompetitive inhibitors were designed and showed activity in primary T cells (Stanford 2011, Vang 2011, He 2013) as a potentially valuable approach in autoimmunity. Ongoing challenges are selectivity and cell permeability of these inhibitors. In addition, these compounds totally inhibit Lyp protein and therefore can affect also the desired functions of the wild type protein.

On this background, it was recently demonstrated the possibility of down-modulating the expression of the wild type PTPN22 gene in the Jurkat human T lymphoblastoid cell line and in human peripheral blood mononuclear cells of healthy individuals by delivering original siRNA duplexes by liposomal formulations (Perri 2017). Liposomal formulations were already utilized in clinical trials, for their minimal toxicity and biodegradability profiles (Opanasopit 2011, Liu 2015, Watts 2012, Dutta 2016, Joly 2011, Kudoh 2011, Petre 2007, Andreakos 2009). Specifically, cationic liposomes composed of the natural lipid dimyristoyl-sn-glycero-phosphatidylcholine (DMPC) and a synthetic cationic gemini surfactant (2S,3S-2,3-dimethoxy-1,4-bis(N-hexadecyl-N,N-dimethylammonium)-butane dibromide (1) or 2R,3S-2,3-dimethoxy-1,4-bis(N-hexadecyl-N,N-dimethylammonium)-butane dibromide (2) (Bello 2006, Bombelli 2010, Bombelli 2005, Bombelli 2005BIS) were employed to deliver lipoplexes against the wild type PTPN22 gene in Jurkat T cells and human peripheral blood lymphocytes of normal subjects (Perri 2017).

The biological effect of PTPN22 down-modulation was confirmed in functional assays (Perri 2017). Confocal microscopy analysis showed that lipoplexes were depicted in both CD3+ and CD3-PBMC. Therefore this shows that the liposomal formulations are suitable for transfecting both B and T lymphocytes. It was observed that in cultures of Jurkat T cells or PBMC from healthy donors (Perri 2017) even cryopreserved PBMC from T1D patients upon transfection with lipoplexes did not reveal signs of toxicity as assessed by cell morphology, viability, quantity and quality of cell pellets and quantification of protein extract concentration at the end of the experimental procedure. However, wild type PTPN22 siRNA cannot be used in therapy, since it silences the wild type PTPN22 gene inhibiting its beneficial functions.

On this background, the present invention provides a specific target down-regulation using novel antisense strand, complementary to the mRNA of the variant PTPN22 gene, which restores the net activity of the normal allele and the normal Lyp regulatory performance.

More specifically, according to the present invention, a novel variant C1858T PTPN22 short interfering RNA duplex (siRNA) is provided which is able to specifically down-modulate the variant PTPN22 allele without silencing the wild type PTPN22 allele. Therefore, siRNA of the present invention can be advantageously used in the prevention and therapy of the autoimmune diseases which are characterized by the PTPN22 variant without affecting the desired functions of the wild type gene. In addition, according to the present invention, the delivery of the siRNA into PBMC of Type 1 diabetes patients has been optimized by using liposomal carriers.

In particular, conformational stability, size and polydispersion of siRNA in lipoplexes was measured by CD spectroscopy and DLS. Lipoplexes internalization and toxicity evaluation was assessed by confocal microscopy and flow cytometry analysis. PBMC were efficiently transfected by stable custom lipoplexes. PBMC morphology was not affected. Lipoplexes incorporation was visualized in CD3+ but also in CD3-peripheral blood immunotypes without signs of toxicity, damage or apoptosis.

The effect of siRNA duplex on Lyp expression was evaluated by means of quantitative Real Time PCR. Liposome/siRNA complexes treatment revealed a significant decrease in target variant PTPN22 mRNA by quantitative Real-Time PCR in a total of 13 out of 16 heterozygous patients (approximately 81,2% of analyzed samples) while there was no effect on wild-type patients as expected.

Interestingly results were confirmed by the analysis with both primers detecting content of target PTPN22 mRNA or solely T1858 variant mRNA.

Functional assays through engagement of TCR signaling were established to evaluate biological consequences of variant PTPN22 down-modulation, as a consequence of restoring the net effect of the wild type allele. A reduced IL-2 production in primary T lymphocytes from PBMC of heterozygous T1D patients was observed, compared with those of wild type T1D patients following T cell receptor (TCR) engagement (FIG. 7). In the experiments described in Example 1, lipoplexes treatment in doses ranging from 60 to 100pmols of siRNA restored in heterozygous, compared to wild-type T1D patients, IL-2 levels of secretion upon 20 hrs of anti-CD3/CD28 PBMC stimulation (FIG. 8). This was also verified using Lipo/siRNA 100pmols in a prolonged time course of anti-CD3/CD8 stimulation that is ideal in exploiting immunomodulation (Perri 2017).

The results of the study show that the selective inhibition of variant PTPN22 allele using lipoplexes of siRNA duplexes can be used in the treatment of autoimmune diseases.

As mentioned before, the PTPN22 variant was also found associated with other diseases, so it is plausible that lipoplexes targeting the PTPN22 variant can find widespread applicability in several autoimmune conditions. For personalized treatment, functionalization of lipoplexes with monoclonal antibodies generated against peculiar immunotypes i.e anti-CD20 Ab to target B lymphocytes, especially involved in some non-organ specific autoimmune diseases i.e. SLE, may additionally be requested whilst sparing tolerogenic B regulatory cells (Breg).

Therefore, it is an object of the present invention a short interfering RNA (siRNA) duplex targeting PTPN22 C1858T single nucleotide polymorphism, said short interfering RNA comprising or consisting of the sequence 5'-AUGAUUCAGGUGUCCAUAC-3' (SEQ ID NO:2) and its complementary sequence 5'-GUAUGGACAC-CUGAAUCAU-3' (SEQ ID NO: 1). SEQ ID NO:1 and 2 of the short interfering RNA duplex according to the present invention can have a dinucleotide at 3' end, wherein said dinucleotide is chosen from the group consisting of dTdT, dAdA, dGdG and dCdC. The dinucleotide is added to increase stability.

According to an embodiment of the present invention, the short interfering RNA duplex can be delivered by a carrier. The carrier can be a liposome, such as a cationic liposome, a nanocarrier, such as solid-lipid nanoparticles, or a PEGylated liposome. Solid-lipid nanoparticles are synthesized by the dispersion of liquid into water or aqueous solution of surfactant. They combine the benefits of liposomes and polymeric nanoparticles for their high stability in physiological environment. PEGylated liposomes are "stealth" liposomes that evade detection and destruction by phagocytes by virtue of their cloaks of hydrated PEG (polyethylene glycol) molecules. Their purpose is two-fold: (1) to increase the bioavailability of drugs or supplements bypassing the digestive tract, and (2) to minimize any potential toxicity or side effects of these agents by remaining in the circulation for a long time and releasing their payloads slowly. As a bonus, they are passively targeted to tumors and to inflamed tissues, where they are preferentially absorbed because of the increased permeability of the capillaries that nourish these tissues.

According to some embodiments of the present invention, the cationic liposome can comprise or consist of dimyristoyl-sn-glycero-phosphatidylcholine (DMPC) in combination with 2R,3S-2,3-dimethoxy-1,4-bis(N-hexadecyl-N,N-dimethylammonium)-butane dibromide, or in combination with 2S,3S-2,3-dimethoxy-1,4-bis(N-hexadecyl-N,N-dimethylammonium)-butane dibromide.

According to the present invention, the carrier can be functionalized with FDA approved monoclonal antibodies against T lymphocytes, such as anti-CD3 otelixizumab (Tolerx and GlaxoSmithKline) and teplizumab (Macrogenics) or against B lymphocytes such as anti-CD20 antibody such as Rituximab (Mabthera®), and antibodies anti-LFA-1 (lymphocyte function-associated antigen 1, CD11a) or anti-LFA-3 (lymphocyte function-associated antigen 3 binding CD2).

According to a further embodiment of the present invention the carrier can be functionalized with a high selectivity and high affinity sialoside analogue for Siglec-based cell targeting, such as sialic acid mimetic (SAM) ligand of the molecule Siglec 10 for cell targeting, for example the sialic acid mimetic (SAM) PEG-lipid-F9 ligand for Siglec-10. A reduced expression of Siglec 10 is indeed reported in Type 1 diabetes and other autoimmune diseases such as rheumatoid arthritis and autoimmune polyglandular syndrome. The mimetic compound can be F9 pegylated lipid (PEG-lipid-F9) prepared for incorporation into liposomal nanoparticles (Rillahan 2012, Bull 2016).

The present invention concerns also a pharmaceutical composition comprising or consisting of short interfering RNA duplex as defined above in association with one or more excipients and/or adjuvants.

A further object of the present invention is the short interfering RNA duplex as defined above or the pharmaceutical composition as defined above, for use as medicament.

In addition, the present invention concerns the short interfering RNA duplex as defined above or the pharmaceutical composition as defined above, for use in the prevention and/or treatment of autoimmune diseases. Particularly, the short interfering RNA duplex or the pharmaceutical composition according to the present invention, can be used in the prevention and/or treatment of autoimmune diseases in a population of subjects carrying the PTPN22 C1858T single nucleotide polymorphism.

The autoimmune diseases can be chosen from the group consisting of insulin-dependent diabetes mellitus (T1D), autoimmune thyroid disease (ATD) (i.e. Graves' disease and Hashimoto's thyroiditis (HT)), myasthenia gravis, multiple sclerosis, systemic lupus erythematosus (SLE), Wegener's granulomatosis, rheumatoid arthritis, juvenile idiopathic arthritis, celiac disease, vitiligo, Sjögren syndrome, primary adrenal insufficiency, alopecia areata, giant cell arteritis, polymyositis.

BRIEF DESCRIPTION OF THE SEVERAL VIEWS OF THE DRAWINGS

The present invention is described by an illustrative, but not limitative way, according to preferred embodiments thereof, with particular reference to the enclosed drawings, wherein.

Plasma membranes are stained with WGA, lipoplexes with PKH26 probe (positive dots, arrows) and nuclei with DAPI. Bars: 10 µm (A, C) and 5 µm (B, D).

For Figure in black and white, arrows in top right panels of A and C indicate PKH26 positive lipoplexes and bottom right panels their internalization in CD3+ and CD3-lymphocytes. Arrows in respective XY-Z orthogonal projections of confocal images (B, D) indicate lipoplexes internalization close to/beneath the cell membrane in CD3+ (B) and CD3- (D) cells.

Figure 11:
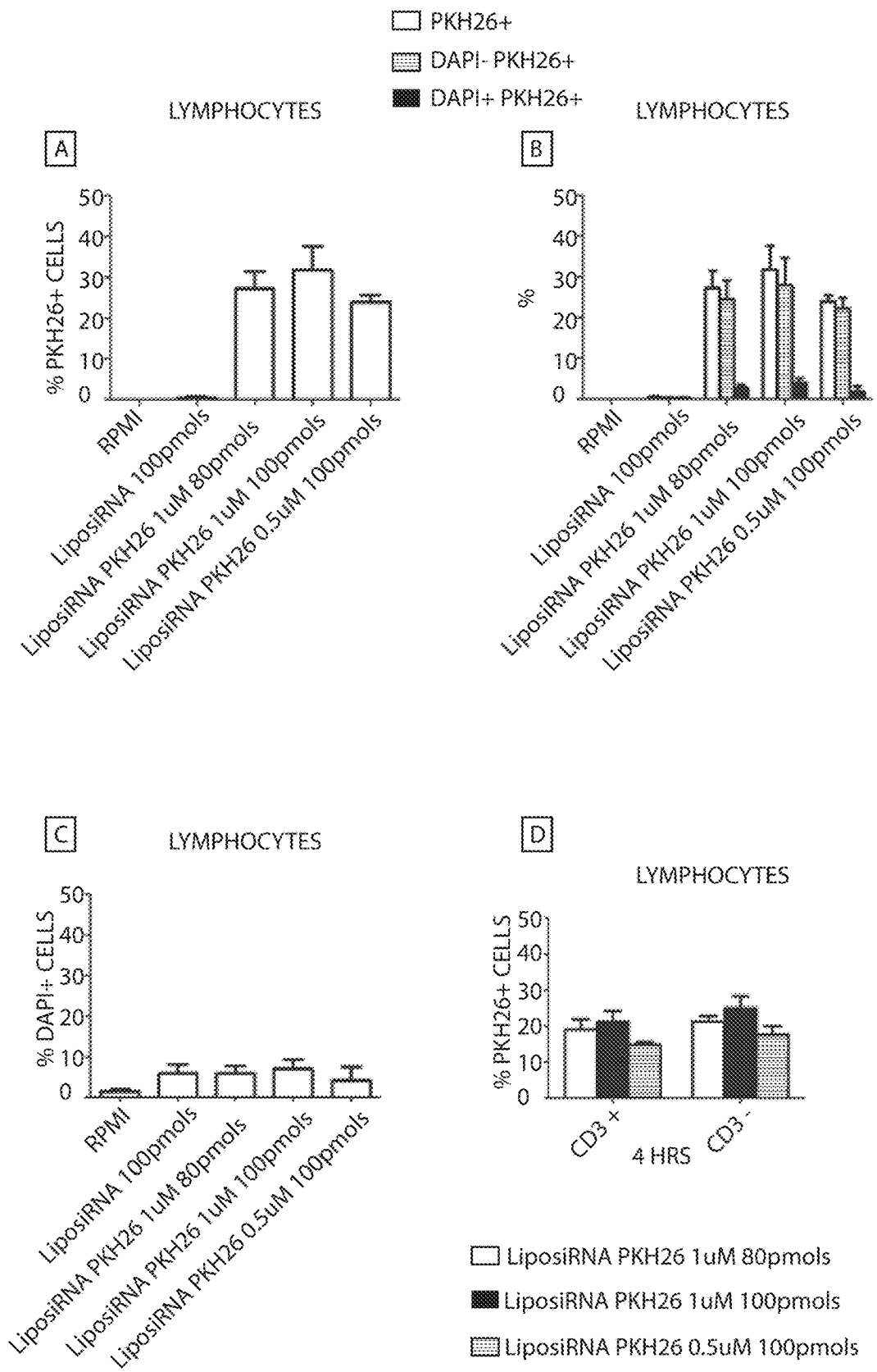

FIG. 11. Evaluation of PKH26-labelled Lipo/siRNA toxicity on HD PBMC. (A) Histogram shows the percentages of total PKH26+ cells among lymphocytes upon the indicated treatments testing Lipo/siRNA labelled with PKH26 (0.1 µM); (B) Histogram shows the percentages of total PKH26+ cells, live PKH26+ cells (DAPI-) and dead PKH26+ cells (DAPI+) among lymphocytes upon the indicated treatments; (C) Histogram shows the percentages of dead cells DAPI+ among lymphocytes upon the indicated treatments; (D) Histogram shows the percentages of total PKH26+ cells among CD3+ and CD3-lymphocytes upon the indicated treatments. The treatment was performed for 4 and a half hours. Bars show the mean±SEM. N=5 healthy donors.

Figure 12:
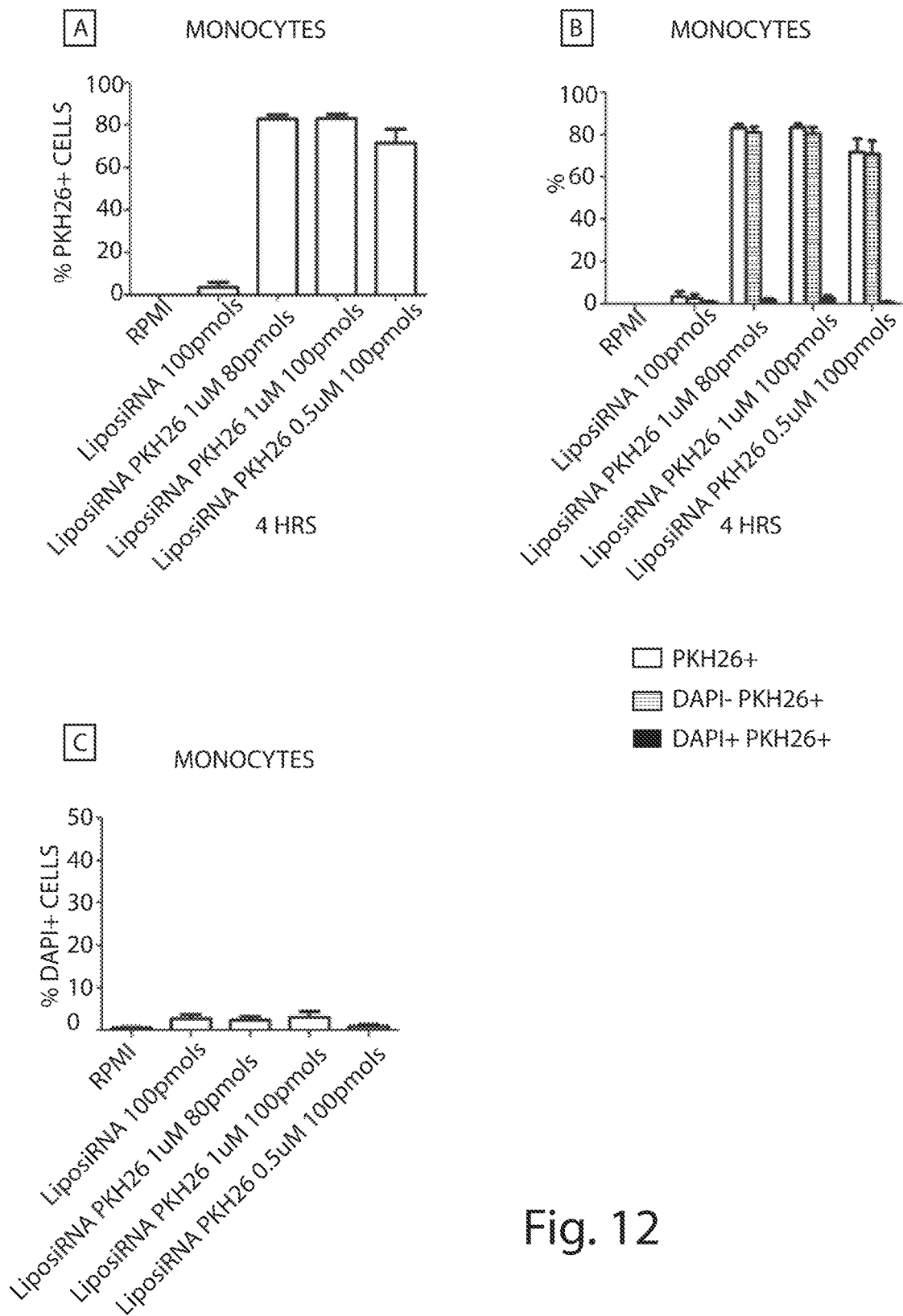

FIG. 12. Evaluation of PKH26-labelled Lipo/siRNA toxicity on monocytes. (A) Histogram shows the percentages of total PKH26+ cells among monocytes upon the indicated treatments; B) Histogram shows the percentages of total PKH26+ cells, live PKH26+ cells (DAPI-) and dead PKH26+ cells (DAPI+) among monocytes upon the indicated treatments; C) Histogram shows the percentages of dead cells DAPI+ among lymphocytes upon the indicated treatments. The treatment was performed for 4 and a half hours. Bars show the mean±SEM. N=5 healthy donors.

Figure 13:
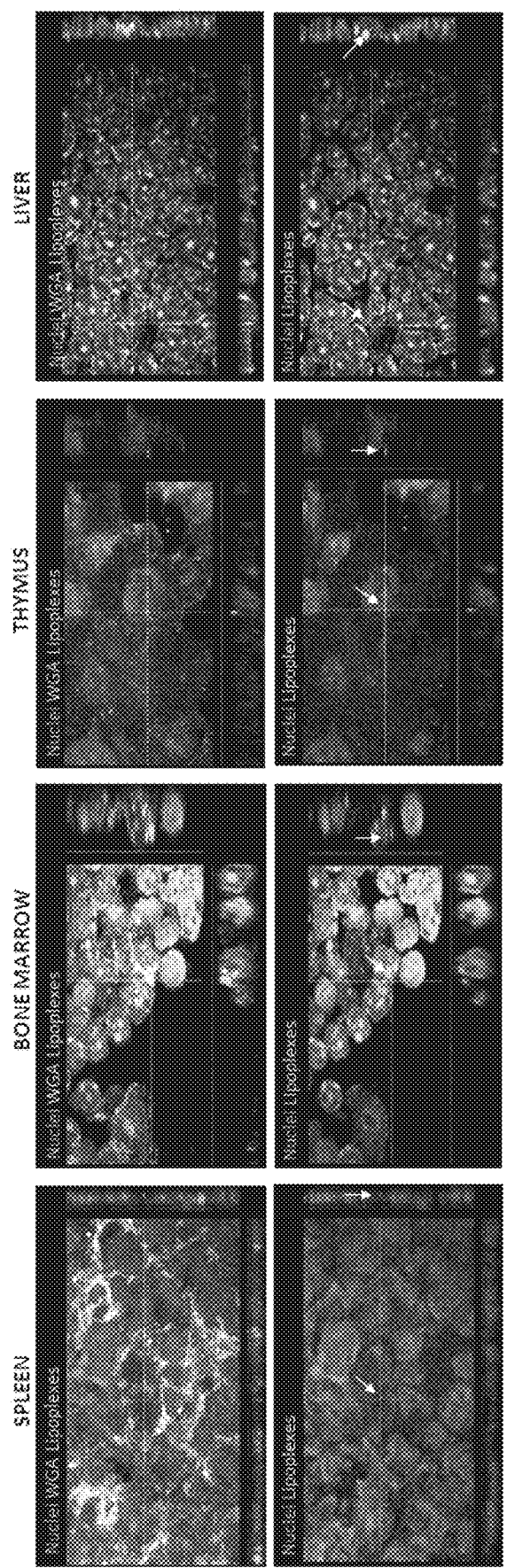

FIG. 13. Preliminar biodistribution study of PKH26-labelled Lipo/siRNA in mice. XY-Z orthogonal projections of confocal microscopy images showing the internalization of siRNA molecules (PKH26 positive dots, arrows) in several murine tissues, as spleen, bone marrow, thymus, liver.

Plasma membranes were stained with wheat germ agglutinin (WGA), lipoplexes with PKH26 probe (positive dots, arrows) and nuclei with DAPI. For Figure in black and white arrows in bottom panels indicate the internalization of lipoplexes in the indicated tissues.

Figure 14:
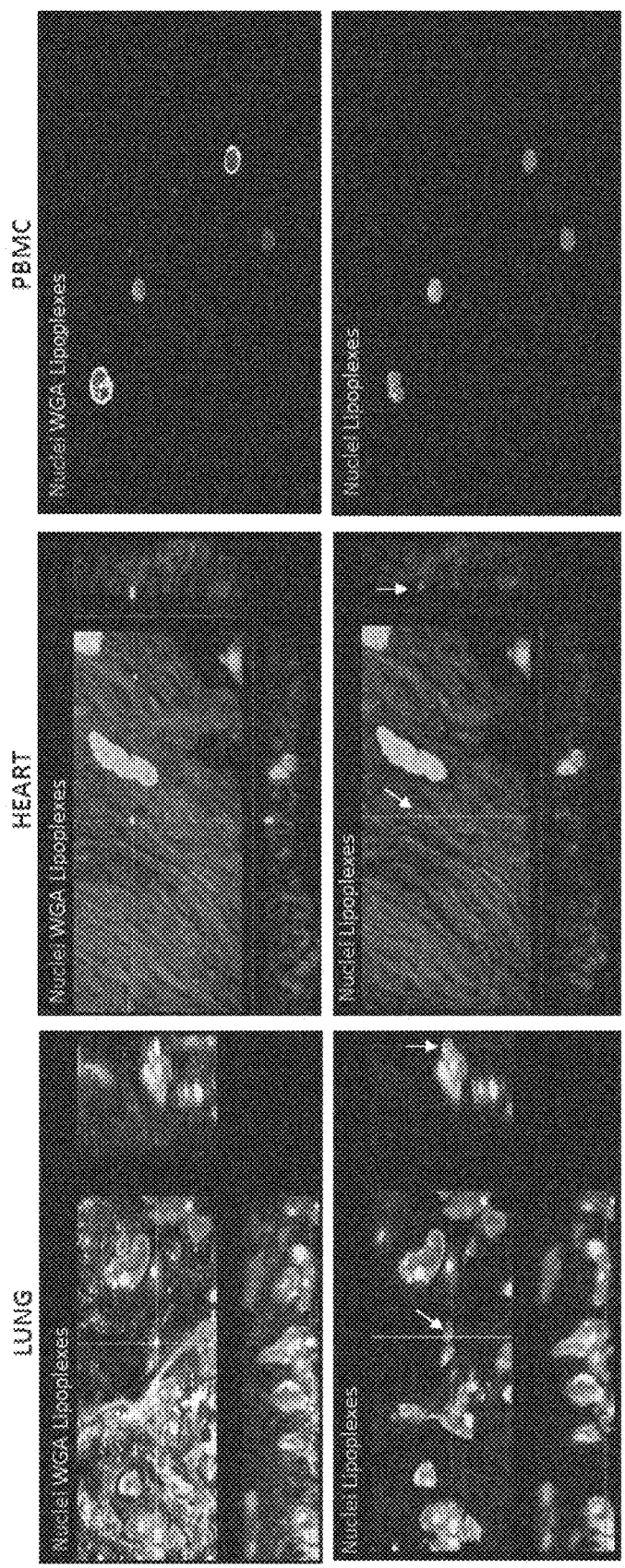

FIG. 14. Preliminar biodistribution study of PKH26-labelled Lipo/siRNA in mice. XY-Z orthogonal projections of confocal microscopy images showing the internalization of siRNA molecules (PKH26 positive dots, arrows) in murine lung and heart, whereas no dots were observed in peripheral blood mononuclear cells (PBMC). For Figure in black and white arrows in bottom panels indicate the internalization of lipoplexes in the indicated tissues.

Figure 15:
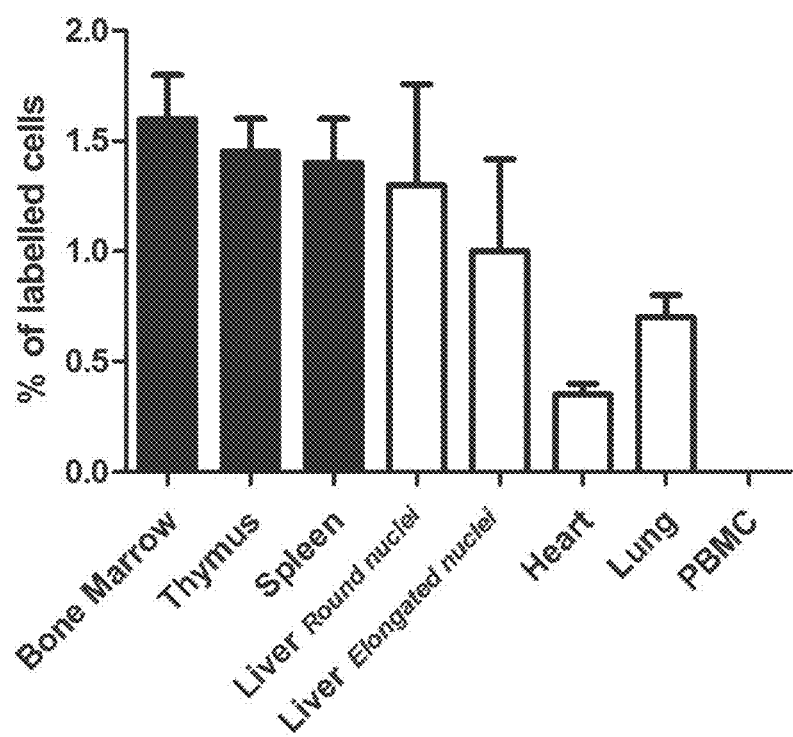

FIG. 15. Preliminar biodistribution study of PKH26-labelled Lipo/siRNA in mice organs. Histogram showing percentages of PKH26-labelled cells within the analysed lymphoid and non-lymphoid organs. 2 subpopulation of cells were identified within the liver: cells with round nuclei and elongated nuclei.

DESCRIPTION OF SPECIFIC EMBODIMENTS OF THE INVENTION

EXAMPLE 1: Study of the delivery of Short Interfering RNA of the present invention by Cationic Liposomes into PBMC of Type 1 diabetes patients and of Down-Regulation of Variant PTPN22 Gene in T Lymphocytes.

Methods

Preparation and Characterization of Liposome Formulations

Gemini surfactant 2R,3S-2,3-dimethoxy-1,4-bis(N-hexadecyl-N,N-dimethylammonium)-butane dibromide, 2, was prepared as previously reported (Bello 2006; Seebach 1977; Aleandri 2012, Perri 2017).

For the preparation of liposome and lipoplex formulations and siRNA stock solution, a freshly prepared buffer solution of 5 mM HEPES and 0.1 mM EDTA, at pH 7.4 (Sigma-Aldrich, Chemical Company (Co.), St Louis, MO) was used.

Liposomes composed of DMPC (purity>99%, Avanti Polar Lipids Inc. (Alabaster, AL)) and 2 at a 50/50 molar percentage were prepared following a previously described procedure (Hope 1992). A film of DMPC (3.0 µmol) and 2 (3.0 µmol) was prepared on the inside wall of a round-bottom flask by evaporation of a CHCl3 solution containing the proper amounts of the component. The film was then dried for 7 hours (hrs) under high vacuum, and 3.0 ml of buffer solution were added to have a final dispersion 1.0 mM in DMPC and 1.0 mM in 2 (Perri 2017). The solution was vortex-mixed, freezed-thawed six times from liquid nitrogen to 313 K, and finally extruded (10 times) through a 100 nm polycarbonate membrane (Whatman Nuclepore, Toronto, ON, Canada). Extrusions were carried out at 40° C., above the DMPC transition temperature (24.2° C.), on a 10 ml extruder (Lipex Biomembranes, Vancouver, Canada). For the preparation of lipoplexes (DMPC/2/siRNA or Lipo/siRNA), proper volumes of the siRNA stock solution (0.1 mM in buffer) were added to a diluted liposome solution to have the final concentrations: [siRNA]=1.3 µM, [DMPC]=50 M, [2]=50 UM, corresponding to a charge ratio+/−=2.

Samples for confocal microscopy were prepared following the same procedure described above, adding a fluorescent probe (1,2-dimyristoyl-sn-glycero-3-phosphoethanolamine-N-(lissamine rhodamine B sulfonyl)-ammonium salt, Avanti Polar Lipids) or PKH26 to the lipid solution, during the film preparation step. The fluorescent probe was used in a 0.1 mol percentage with respect to DMPC. Samples were analyzed by circular dichroism spectroscopy (CD) and dynamic light scattering (DLS) at different times after the preparation (9, 24, 48, 72 hrs) (Perri 2017).

Circular Dichroism Spectroscopy

CD spectra were recorded on a Jasco spectropolarimeter J-715 equipped with a Peltier device for the temperature control, using 0.5 cm path length quartz cuvettes. Measurements were run in the 330-220 nm spectral range at 25° C.

5'-GUAUGGACACCUGAAUCAU-3' (SEQ ID NO: 1) with dTdT at 3' end; SNP_T antisense 5'-AUGAUUCAG-GUGUCCAUAC-3' (SEQ ID NO: 2) with dTdT at 3' end, Sigma Chemical Co.). dTdT was added in order to increase stability. Alternatives for any below cited sequence could be dAdA, dGdG and dCdC. Table 1 shows the design of duplex siRNAs SNP_T (sense and antisense) against the variant T1858 PTPN22 allele.

TABLE 1

| Target Name | Sense/ Antisense | SIRNA Design wherein each sequence has dTdT at 3' end | Start | Target Sequence |
|---|---|---|---|---|
| SNP_T | s | GUAUGGACACCUGAAUCAU (SEQ ID NO: 1) | 45 | GTATGGACACCTGAATCAT (SEQ ID NO: 11) |
| SNP_T | a | AUGAUUCAGGUGUCCAUAC (SEQ ID NO: 2) | 45 | ATGATTCAGGTGTCCATAC (SEQ ID NO: 12) |
| SNP_T | s | CUUCCUGUAUGGACACCUG (SEQ ID NO: 3) | 39 | CTTCCTGTATGGACACCTG (SEQ ID NO: 13) |
| SNP_T | a | CAGGUGUCCAUACAGGAAG (SEQ ID NO: 4) | 39 | CAGGTGTCCATACAGGAAG (SEQ ID NO: 14) |
| SNP_T | s | AUGGACACCUGAAUCAUUU (SEQ ID NO: 5) | 47 | ATGGACACCTGAATCATTT (SEQ ID NO: 15) |
| SNP_T | a | AAAUGAUUCAGGUGUCCAU (SEQ ID NO: 6) | 47 | AAATGATTCAGGTGTCCAT (SEQ ID NO: 16) |
| SNP_T | s | UGUAUGGACACCUGAAUCA (SEQ ID NO: 7) | 44 | TGTATGGACACCTGAATCA (SEQ ID NO: 17) |
| SNP_T | a | UGAUUCAGGUGUCCAUACA (SEQ ID NO: 8) | 44 | TGATTCAGGTGTCCATACA (SEQ ID NO: 18) |
| SNP_T | s | UAUGGACACCUGAAUCAUU (SEQ ID NO: 9) | 46 | TATGGACACCTGAATCATT (SEQ ID NO: 19) |
| SNP_T | a | AAUGAUUCAGGUGUCCAUA (SEQ ID NO: 10) | 46 | AATGATTCAGGTGTCCATA (SEQ ID NO: 20) |

CD spectra are the average of 16 scans obtained with an instrument scanning speed of 100 nm/min, response time of 1 second(s) and resolution of 1 nm (Perri 2017).

Dynamic Light Scattering

DLS measurements were obtained with a Brookhaven Instruments Corp.BI-200SM goniometer equipped with a BI-9000AT digital correlator using a solidstate laser (125 mW, λ=532 nm). Unless otherwise stated, measurements of scattered light were made at a scattering angle θ of 90°. Measurements were carried out at 25° C. (Perri 2017) and temperature was controlled with an accuracy of 0.1° C. Each experiment (duration in the range of 5-20 minutes) was repeated two or more times. CONTIN algorithm was used to fit the data.

siRNA design siRNA sequences were originally designed specifically for the target C1858T PTPN22 gene variant. These have been generated using a siRNA design algorithm licensed from Rosetta Inpharmatics (Sigma-Aldrich Chemical Co., sigma_aldrich_dot_com_life-science_functional-genomics-and-rnai_RNA_learning-center).

From a list of siRNA sense/antisense (s/a) duplexes differing in mRNA target affinity (Table 1), generated without any backbone modification, the specific sequence with the higher affinity for the target was chosen for subsequent experiments, namely siRNA sequence (SNP_T sense C1858T PTPN22 Gene Variant Silencing in Human PBMC.

Study Population

The study population was composed of 22 long-term T1D patients who were referred from the Department of Endocrinology at Bambino Gesu' Children's Hospital (OPBG). Of the total number of long-term patients, 16 were carriers of the C1858T PTPN22 polymorphism in heterozygosis, and 6 were non-carriers.

All enrolled patients were unrelated. All subjects entered the investigation after obtaining written informed consent. The study was approved by the local Institutional Review Board (IRB) of Bambino Gesu' Children's Hospital, regulating the use of human samples for experimental studies (N°1385). The informed consent for children was obtained from the next of kin. Consent on behalf of children was written. Participant consent was recorded using a paper-based inventory system. The IRB approved the consent procedure.

Detection of the C1858T Variant in the PTPN22 Gene

Molecular analysis of the C1858T (R620W) polymorphism of the autoimmunity predisposing gene PTPN22 was evaluated in the DNA of patients and controls using a Xcml restriction fragment length polymorphism-PCR (polymerase chain reaction) method (Bottini 2004, Gianchecchi 2013).

Cell Preparation

Peripheral blood mononuclear cells (PBMC) were separated by Ficoll-Hypaque (Histopaque, Sigma-Aldrich Chemical Co.) from sodium heparinized venous blood samples (5-10 ml) of recruited T1D patients. Subsequently, PBMC were frozen down in liquid nitrogen according to standard protocols (Gianchecchi 2014).

Custom Liposome Transfection Protocol

T1D PBMC were thawed, washed in complete RPMI 1640 medium (EuroClone, Pero (Milan), Italy) supplemented with 10% fetal bovine serum (FBS, GE Healthcare Life Sciences, UT, USA) and L-glutamine (2 mM) (Euro-Clone). PBMC were then seeded at $1.5 \times 10^6$ cells per well in 48-well plates (Falcon, Corning, NY, USA) in a final volume of 250 µl of FBS-free RPMI 1640 medium supplemented with L-glutamine (2 mM) and treated with different doses of Lipo/siRNA complexes (20, 60, 80, 100 pmols of siRNA). After an overnight (O/N) transfection, cells were washed by centrifugation at 1200 rpm for 5 minutes, seeded again in 48 wells flat bottom plates in complete RPMI medium at a final volume of 250 µl and incubated at 37° in a humidified atmosphere containing 5% $CO_2$ for additional 24 and 48 hrs corresponding to a final transfection time of 48 and 72 hrs respectively.

Rna Extraction and Quantitative Real Time-PCR Analysis

Total RNA from untreated or treated PBMC was isolated with TRIzol™ Reagent (Invitrogen, Life Technologies Corporation, Carlsbad, CA, USA) following the manufacturer's instructions. After in vitro reverse transcription (500 ng) with the High-Capacity cDNA reverse transcription kit (Applied Biosystems, Foster City, CA), quantitative Real-Time PCR (rtq-PCR) was performed using 7900HT Fast Real-Time PCR System (Applied Biosystems) and Power SYBR Green PCR Master Mix (Applied Biosystems) with the following primers:

(i) GAPDH (glyceraldehyde-3-phosphate dehydrogenase) (human)
forward (fwd): 5'-CGACCACTTTGTCAAGCTCA-3' (SEQ ID NO:21)
reverse (rev): 5'-AGGGGTCTACATGGCAACTG-3' (SEQ ID NO:22)

(ii) PTPN22 (human)
fwd: 5'-GCTGTACTAGCAACTGCTCC-3' (SEQ ID NO:23);
rev: 5'-CCAGCTTCCTCAACCACAAT-3' (SEQ ID NO:24)

(iii) PTPN22T1858 (human)
fwd: 5'-CAGCTGTACTAGCAACT-3' (SEQ ID NO:25)
rev: 5'-AGGTGTCCATACAGGAA-3' (SEQ ID NO:26)

For the analysis, the mRNA levels, normalized to GAPDH, were calculated as follows:

$$2^{-[\Delta Ct(Lipo/siRNA) - \Delta Ct(RPMI)]} = 2 - \Delta\Delta Ct,$$

where $\Delta Ct = C_t$ (PTPN22 or PTPN22T1858)-$C_t$ (GAPDH).

Rtq-PCR products were purified by means of a Gel and PCR clean up kit (Qiagen, Hilden, Germany) following the manufacturer's instructions and subsequently analyzed using the Genetic Analyzer 3500 (Applied Biosystems).

Confocal Microscopy Analysis

T1D PBMC from both wild-type and heterozygous patients were seeded at $1.5 \times 10^6$ cells per well in 48-well plates (Falcon) in a final volume of 250 µl of FBS-free RPMI 1640 medium (EuroClone) supplemented with L-glutamine (2 mM) (EuroClone) and treated with Lipo/siRNA complexes marked with rhodamine (100 pmols of siRNA) for 4 and a half hrs. At the end of the incubation period, cells were harvested, washed in PBS, and fixed with 4% paraformaldehyde (Sigma-Aldrich Chemical Co.). Fixed cell suspensions were distributed drop wise onto positive charged microscope slides (Super Frost plus, Menzel-Glaser, Germany) and dried at 37° C. After rehydration in PBS, cell permeabilization was obtained incubating microscope slides with 0.1% PBS-Triton X-100 (Sigma-Aldrich Co.) for 5 minutes. Subsequently, 30 minutes blocking with 5% BSA (Bovine Serum Albumin, Sigma-Aldrich Co.) was performed and cells were then stained with primary mouse anti-human CD3 (Clone UCHT1 BD Biosciences, San Jose, CA, 1:30, incubated for 1 hour at room temperature (RT)) followed by secondary antibody (Ab) goat anti-mouse Cy-5 conjugate (Invitrogen, 1:100, incubated for 1 hour at RT). Finally, to counterstain plasma membrane and nuclei, WGA conjugated to Oregon Green1488 (Invitrogen, 1:200) and Hoechst 33342 (Invitrogen, 1 µg/ml) or DAPI (4',6-diamidino-2-phenylindole) were used respectively. Confocal imaging was performed on an Olympus Fluoview FV1000 confocal microscope equipped with FV10-ASW version 2.0 software, Multi Ar (458±488 and 515 nm), 2× He/Ne (543 and 633 nm), and 405-nm diode lasers, using a 60× (1.40 NA oil) objective. Optical single sections were acquired with a scanning mode format of 1024×1024 pixels, sampling speed of 40 ms/pixel (pixel size of 0.2 mm), and Z-reconstructions of serial single optical sections were carried out with an electronic zoom at 2.5. Fluorochromes unmixing was performed by acquisition of automated-sequential collection of multi-channel images, in order to reduce spectral crosstalk between channels (Perri 2017).

Toxicity Assay

Toxicity evaluation of lipoplexes was assessed by monitoring cell morphology, viability, quantity and quality of cell pellets and quantification of protein extract concentration at the end of the experimental procedure. T1D PBMC were seeded at $1.5 \times 10^6$ cells per well in 48-well plates (Falcon) in a final volume of 250 µl of FBS-free RPMI 1640 medium (EuroClone) supplemented with L-glutamine (2 mM) (EuroClone) and treated with different doses of Lipo/siRNA complexes marked with rhodamine (20, 60, 80, 100 pmols of siRNA) for 4 and a half hrs. Subsequently the cells were harvested with complete medium, centrifuged 1200 rpm for 5 minutes, washed once in PBS and resuspended in PBS 2% FBS. To detect and quantify dead cells the blue fluorescent cell impermeant dye DAPI (4',6-diamidine-2'-phenylindole dihydrochloride, Invitrogen) was added at a final concentration of 0.2 µM, 5 minutes prior to analysis of cells by flow-cytometer BD LSR Fortessa X-20 (BD, Sunnyvale, CA). DAPI specifically enters only dead cells when used on live cells. 20,000 events were acquired and data analyzed by BD FACSDiva software 8.0 (BD Biosciences). The evaluation was carried out on triplicate biological determinations.

Functional Assay

A functional assay was implemented to verify the effect of lipoplexes on T cell activation by evaluating interleukin 2 (IL-2) concentration in supernatants of patients PBMC transfected O/N with different doses of Lipo/siRNA complexes (Lipo/siRNA complexes 60, 80 and 100 pmols of siRNA) then treated with Dynabeads Human T-activator CD3/CD28 beads (Invitrogen). After transfection, cells were washed by centrifugation, seeded $2.5 \times 10^5$ per well in 96 wells flat bottom plates in complete RPMI medium, then activated with the indicated anti-CD3/CD28 beads at different bead-to-cell ratios. Cells were subsequently incubated at 37° in a humidified atmosphere containing 5% $CO_2$ for 20 hrs. In an additional experimental condition to specifically address immunomodulation, cells were stimulated with a suboptimal bead-to-cell ratio 1:50 carried out for 5 days (Perri 2017). At the end of the incubation period, supernatants and cells were collected and separated by centrifugation at 1200 rpm for 5 minutes. The concentration of IL-2 in supernatants was estimated by means of the human IL-2

ELISA development kit (Mabtech, Nacka strand, Sweden) following the manufacturer's guideline. Plates were then read at 405 nm by Bench-mark Plus microplate spectrophotometer (Bio-Rad, CA). The evaluation was carried out with at least triplicate biological determinations.

Statistical Analysis

Differences between siRNA+CD3+ and siRNA+CD3- cells, among wild-type and heterozygous T1D PBMC, representing the population's specific transfection efficiency, were statistically evaluated using the unpaired t test. The analysis was performed scoring a total of 600 cells by two independent observers (MP, SP). A resulting P value <0.05 was considered statistically significant. For the Lipo/siRNA efficacy experiments, evaluated in rtq-PCR and IL-2 ELISA assays, differences between each test condition and the control condition were assessed for statistical significance with one-way ANOVA analysis of variance and Bonferroni multiple comparison test. To analyze the difference of IL-2 production in functional assays between wild-type and heterozygous C1858T PTPN22 stimulated T1D PBMC unpaired t test was used. The statistical study was performed analyzing multiple biological determinations with GraphPad Prism software version number 5 (San Diego, CA).

Preliminar Biodistribution Studies

Evaluation of Internalization of PKH26-Labelled Lipo/siRNA in Human PBMC.

Following the same procedure reported for rhodamine marked Lipo/siRNA lipoplexes (vide supra) PBMC were treated with Lipo/siRNA complexes marked with PKH26 (0.5-1 µM with 80-100 pmols of siRNA) for 4 and a half hrs. Internalization was evaluated by confocal microscopy analysis as above described.

Evaluation of Toxicity of PKH26-Labelled Lipo/siRNA for In Vivo Studies in Mice.

Lipo/siRNA complexes marked with PKH26 (0.5-1 µM with 80, 100 pmols of siRNA) were administered for 4 and a half hrs. Cell morphology was assessed as above described.

Preliminary Biodistribution Studies of PKH26-Labelled Lipo/siRNA in Mice.

PKH26-labelled PEGylated lipoplexes with 50 µg of siRNA were injected intravenously in a C56BL6 8 weeks old male mice via lateral tail vein in 80 µl volume of Hepes 5 mM/EDTA 0.1 mM, pH 7.4. 24 hrs after injection, the animal was sacrificed by cervical dislocation. For histological analysis under confocal microscopy lymphoid organs spleen, bone marrow, thymus and nonlymphoid organs liver, heart and lung were removed and snap frozen with Optical Cutting Temperature (OCT) method. Peripheral blood samples were also taken in EDTA.

Histological Analysis

Serial 10 µM thick cryostatic sections were cut from frozen tissue blocks. Cytospun slides were prepared from mice PBMC, isolated under Ficoll-Hypaque procedure (Histopaque, Sigma-Aldrich Chemical: St Louis, MO, USA); cells were fixed in 4% paraphormaldehyde, then dropped onto microscopic slides. For microscopic examination plasma membrane and nuclei were stained with WGA conjugated to Oregon Green1488
(Invitrogen, 1:200) and Hoechst 33342 (Invitrogen, 1 µg/ml) respectively. Confocal microscopy analysis was carried out as above described. Cells identified by PKH26-lipoplexes were counted by two independent observers under Nikon Eclipse E600 Optical microscope by scoring at least 1000 elements onto two consecutive sections at 60× magnification under oil immersion.

Results

Evaluation of Size and Polydispersion of Liposomes and Lipoplexes by DLS Measurements DLS experiments on the liposome formulation of DMPC/2 and on lipoplexes (DMPC/2/siRNA or Lipo/siRNA) were performed as previously reported (Perri 2017). The investigations on the liposomes formulation confirmed what it was already described: liposome formulation of DMPC/2 shows a narrow single population centered at about 40 nm after 9 hrs from the extrusion, whereas, after 72 hrs from the preparation, DMPC/2 liposomes increase significantly in dimensions (Perri 2017).

The lipoplexes composed of the siRNA against the variant PTPN22 with the liposomes of DMPC/2 show a behavior similar to that observed for lipoplexes of wild type siRNA (Perri 2017). In fact, also in this case lipoplexes dimensions do not seem to be heavily affected by the presence of siRNA, the dimensions being around 70 nm in diameter. In addition, the lipoplexes DMPC/2/siRNA do not change considerably with time, increasing slightly up to ~90 nm, thus suggesting that lipoplexes are rather stable.

Cd Investigations into the Conformational Stability of siRNA in Lipoplexes

CD investigations of the lipoplexes composed of the siRNA against the variant PTPN22 with the liposomes of DMPC/2 were performed following the same approach previously described for wild type siRNA (Perri 2017). Also in this case, the CD spectrum of siRNA in lipoplexes (DMPC/2/siRNA or Lipo/siRNA), measured at different times after their preparation, resembles that of free siRNA in buffer solution, the bands of lipoplexes being less intense than those of free siRNA. These observations indicate that the association between liposomes and siRNA does not affect significantly the conformational stability of siRNA designed against the variant PTPN22. In addition, the absence of marked variations in the CD spectrum over a 72 hrs period is an indirect confirmation of lipoplexes stability.

Lipo/siRNA SNP_T Lipoplexes are Effectively Internalized in T1D PBMC

Figure 1:
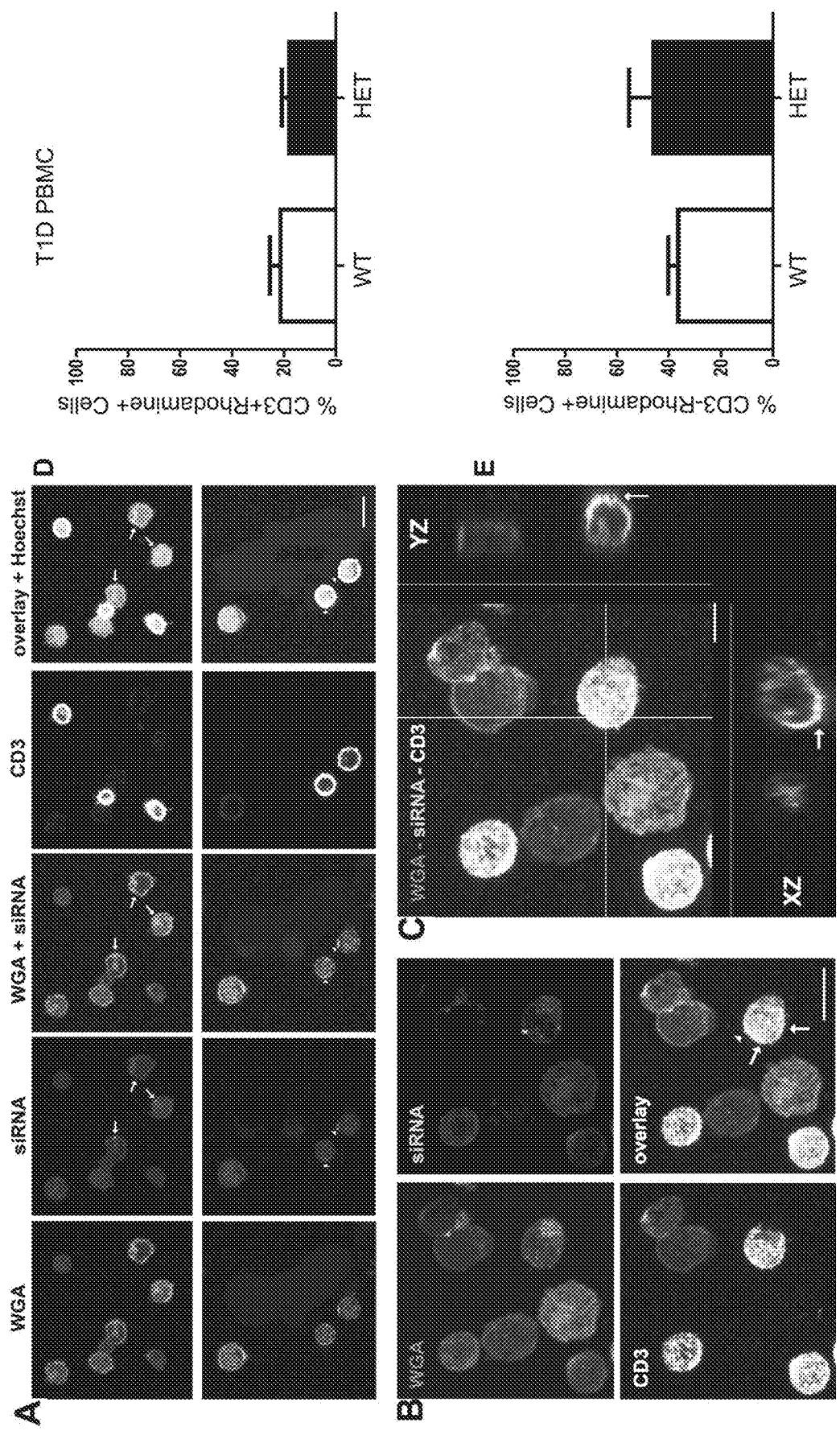
FIG. 1. Confocal microscopy analysis of Lipo/siRNA internalization in TID PBMC. (A) Images shown reveal the presence of lipoplexes (siRNA/red dots and white arrows) inside CD3+ (white) and (B) CD3-cells among PBMC of TID patients already after 4 and half hrs of treatment (100 pmols). WGA (wheat germ agglutinin) is used to stain the cell membrane and cells nuclei are counterstained with Hoechst dye. Bar: 20 μm. (C) Confocal Z reconstructions show the presence of the lipoplexes (indicated by arrows) inside the cytoplasm of CD3+ cells. Bar: 10 μm. (D) Histogram shows the analysis of the percentage of siRNA+ cells (rhodamine+ cells) among wild-type (WT) and heterozygous C1858T PTPN22 (HET) CD3+ and (E) CD3-cells.

Internalization of rhodamine-conjugated Lipo/siRNA complexes (100 pmols of siRNA) was visualized in T1D PBMC following 4 and a half hrs of incubation (FIG. 1, A and B; dots/white arrows indicate lipoplexes; WGA and Hoechst stains indicate membrane and nuclei respectively). Analysis of X-and Y-axis projections of Z-reconstructions of confocal single optical sections (FIG. 1, C) allowed clear detection of lipoplexes beneath the cell membrane. The presence of rhodamine fluorescence inside cells further indicates the efficacy of this delivery system in the internalization of siRNA molecules inside T1D PBMC, as previously observed for Jurkat T cells and healthy donor PBMC (Perri 2017). This result was reported in both wild-type and C1858T PTPN22 heterozygous T1D PBMC (FIG. 1, D and E).

The internalization was confirmed specifically in both CD3+ (white) and CD3-T lymphocytes (FIG. 1, A, B and C). Of notice, no statistically significant difference was observed regarding lipoplexes internalization efficacy between the CD3+ (FIG. 1, D) or CD3-(FIG. 1, E) cells when analyzing wild-type versus (vs) C1858T PTPN22 heterozygous T1D PBMC (FIG. 1, D and E).

Lipo/siRNA SNP_T Lipoplexes are not Toxic to T1D PBMC

PBMC treated with rhodamine-marked lipoplexes (20, 60, 80 and 100 pmols of siRNA) did not show signs of toxicity during the culture period as assessed by quality and quantity of cell pellet and quantification of protein extract concentration at the end of the experimental procedure.

Figure 2:
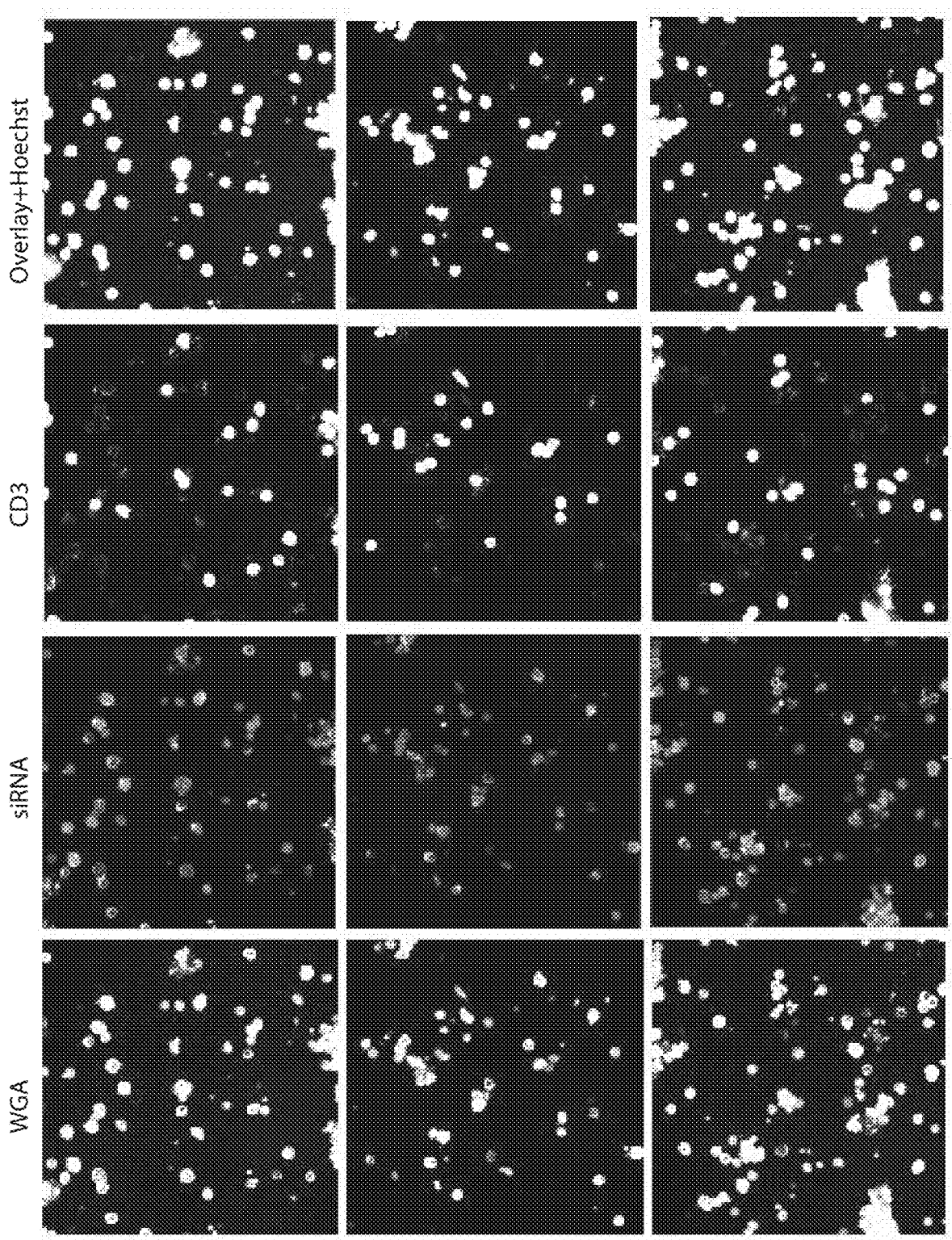
FIG. 2. Lipo/siRNA internalization in TID PBMC. Representative images showing cell morphology in respect to the cell membrane (WGA) and to the cell nuclei (Hoechst). CD3 positivity is shown in white. Transfected cells are siRNA+ (red dots). Bar: 20 μm.

T1D PBMC treated with different doses of rhodamine-conjugated lipoplexes for 4 and a half hrs retained proper morphology both of the cell membrane and of the nuclei as revealed by confocal microscopy (FIG. 2). These cell compartments did not show signs of damage or apoptosis respectively (FIG. 2).

Figure 3:
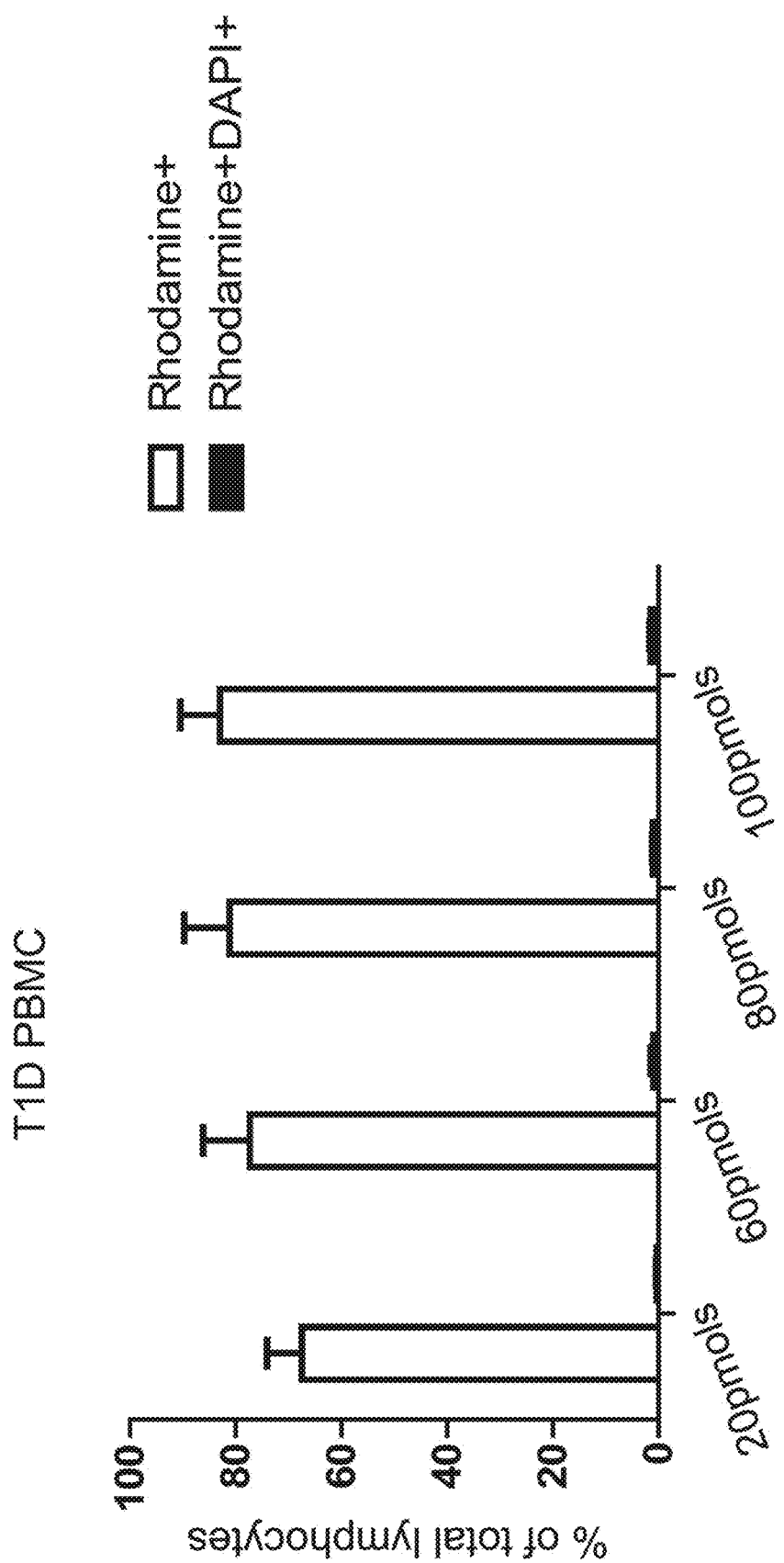
FIG. 3. Evaluation of Lipo/siRNA toxicity on T1D PBMC. Flow cytometry analysis of T1D PBMC from wild-type PTPN22 and heterozygous C1858T PTPN22 patients treated for 4 and half hrs with rhodamine-conjugated lipoplexes (100 pmols). Histogram reveals both the percentage of transfected lymphocytes (rhodamine+ cells) and the relative percentage of dead cells (rhodamine+DAPI+ cells) among the transfected cells.

In Flow-cytometry analysis, T1D PBMC revealed high percentage of rhodamine+ cells implying relevant transfection efficacy and internalization and, at the same time, showed low percentage of dead cells (Rhodamine+DAPI+ cells) (FIG. 3) indicative of low lipoplexes toxicity at this specific timing of the experimental procedure.

Lipo/siRNA SNP_T Lipoplexes Treatment Downregulates PTPN22 mRNA

Figure 4:
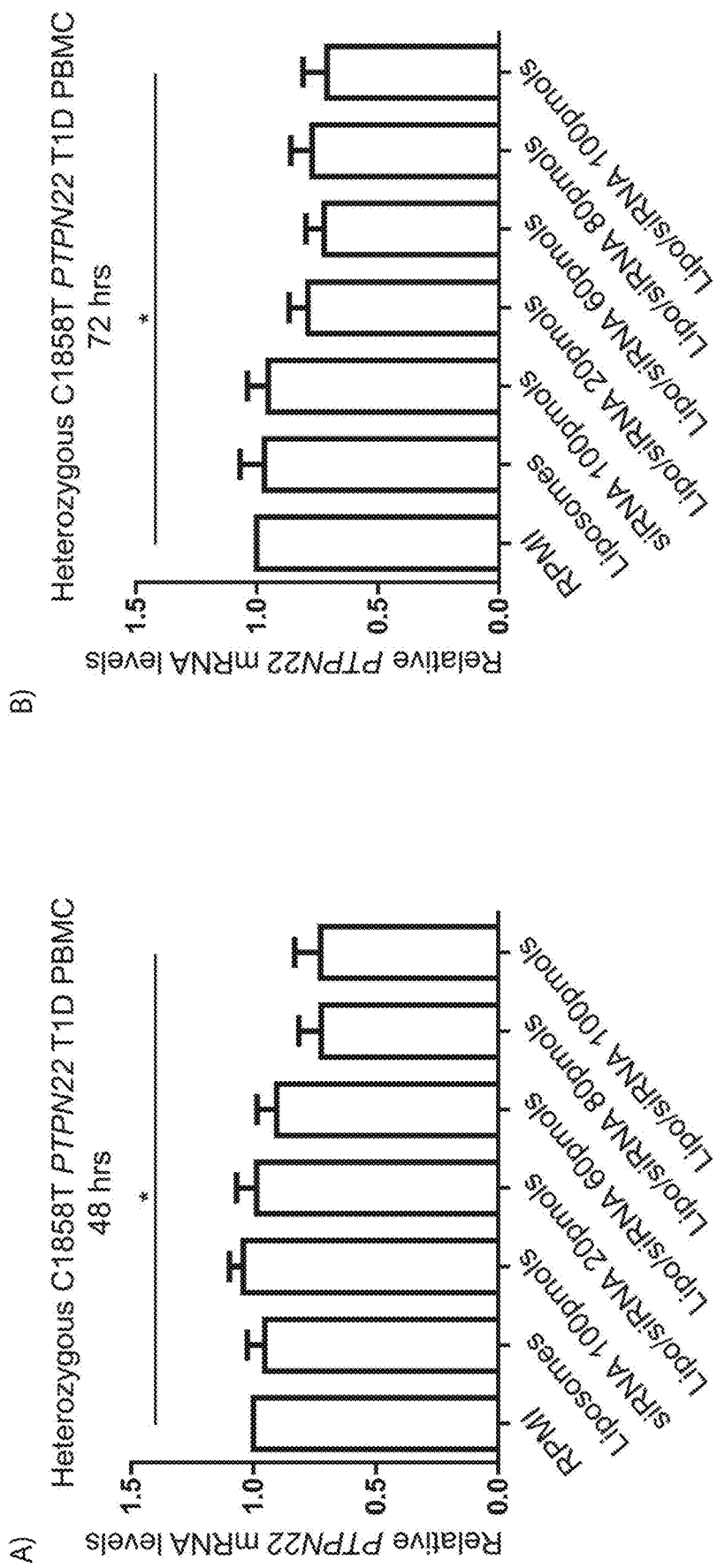
FIG. 4. Overall analysis of Lipo/siRNA efficacy on target mRNA. (A) Histogram comprises the target mRNA analysis deriving from all 16 heterozygous C1858T PTPN22 patients tested including 3 not-responders at 48 and (B) 72 hrs after the indicated treatments. * indicates one-way analysis of variance P value=0.0126 at 48 hrs and P value=0.0401 at 72 hrs.
Figure 5:
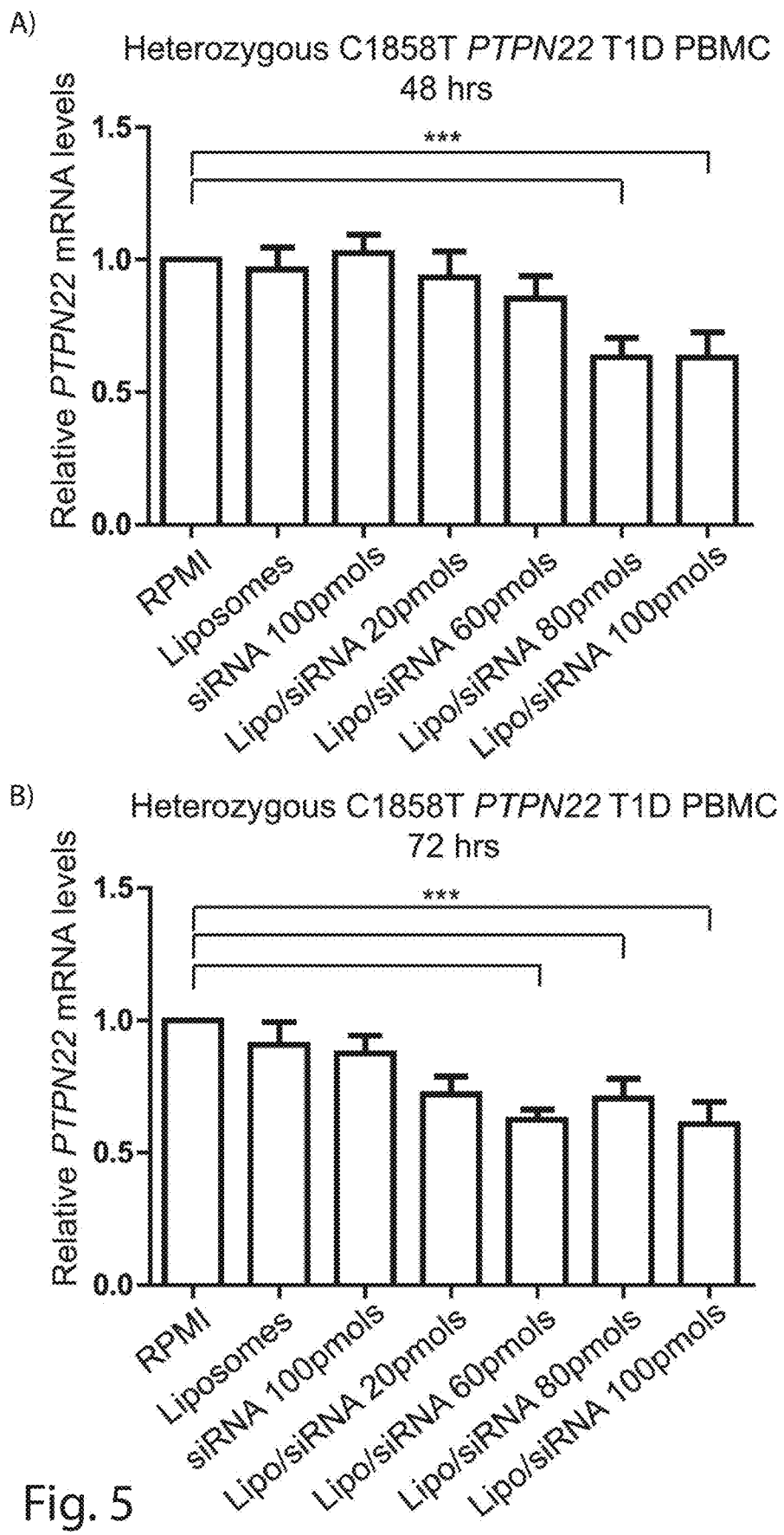
FIG. 5. Assessment of Lipo/siRNA efficacy on target mRNA. (A) Histogram shows significant decrease in target PTPN22 mRNA analyzed by rqt-PCR after treating T1D PBMC with the indicated doses of lipoplexes for 48 hrs. (B) Similar inhibition after 72 hrs was achieved. Statistical test was performed analyzing 13 responder heterozygous C1858T PTPN22 patients. *** indicates one-way analysis of variance P value=0.003 for the data corresponding to the 48 hrs and P=0.002 for the 72 hrs data. (C) Histogram related to the 6 wild-type PTPN22 patients shows no effect on the target mRNA levels at 48 hrs of treatment. (D) No effect was similarly observed after 72 hrs.
Figure 5:
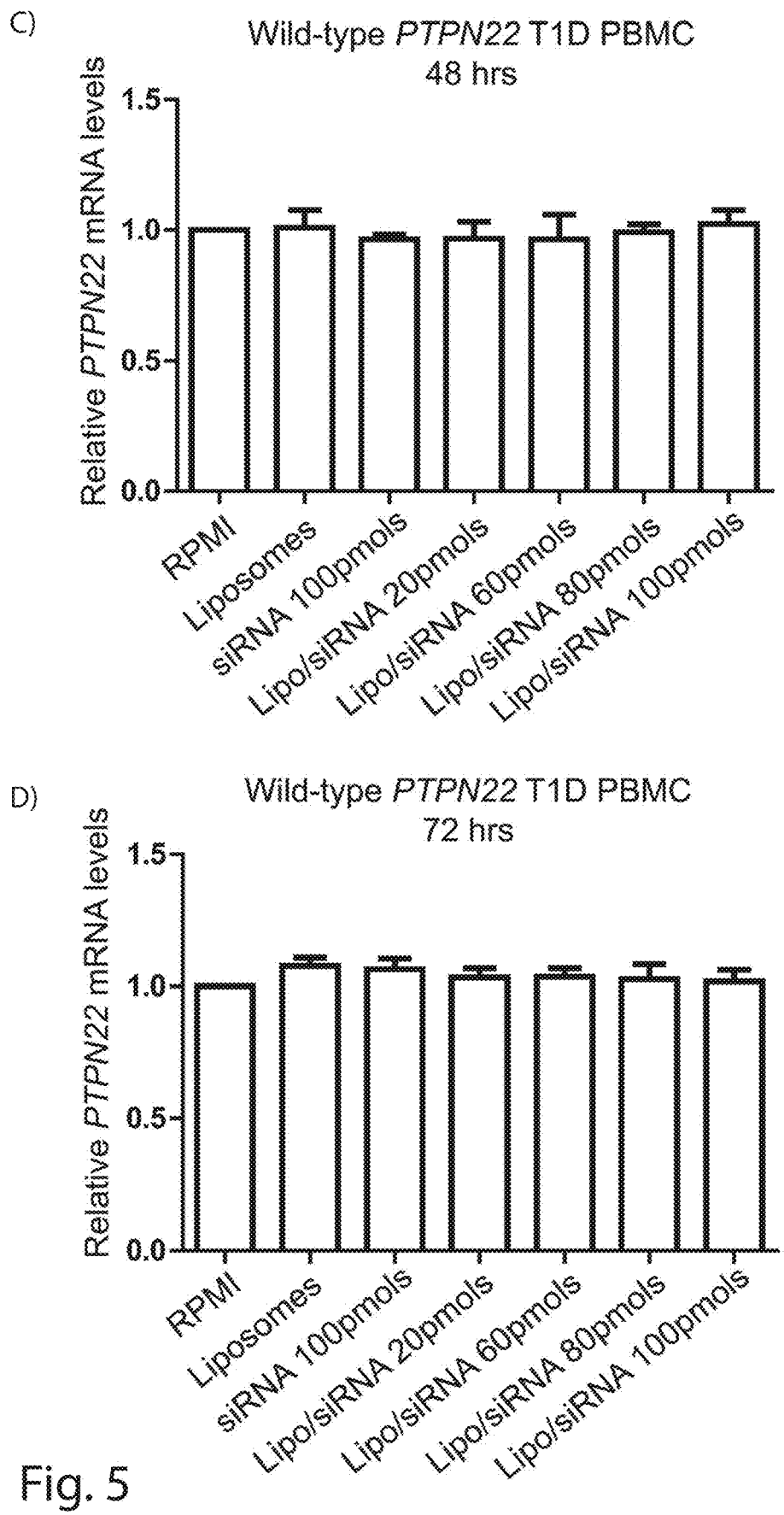

The MRNA obtained from PBMC derived from 16 heterozygous C1858T PTPN22 patients and 6 wild-type PTPN22 patients was analyzed by rtq-PCR after treating cells with different doses of lipoplexes (20, 60, 80 and 100 pmols of siRNA) for 48 and 72 hrs. Either time point of the lipoplexes treatment led to a decrease in the target PTPN22 mRNA levels in 13 out of 16 heterozygous patients (FIG. 5; FIG. 4), while it did not affect the mRNA levels in the wild-type patients (FIG. 5). These results indicate valuable efficacy of the lipoplexes under study to specifically downregulate variant T1858 PTPN22 mRNA.

Figure 6:
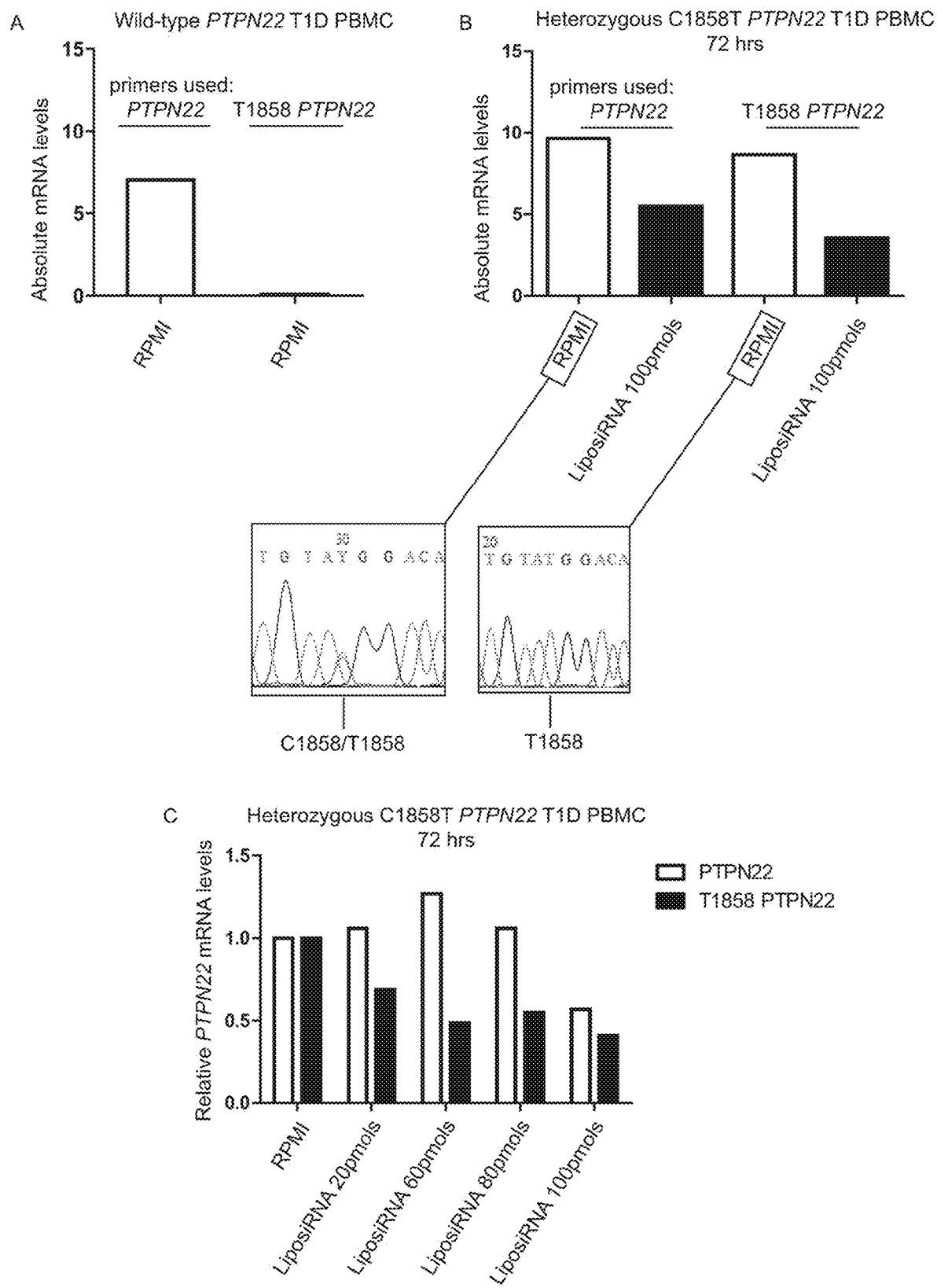
FIG. 6. Evidence for Lipo/siRNA specificity toward T1858 PTPN22 mRNA. (A) Rtq-PCR analysis of mRNA from wild-type PTPN22 T1D PBMC using two different set of primers to recognize whole target PTPN22 gene or T1858 PTPN22 mRNA. (B) Rtq-PCR analysis of mRNA from heterozygous C1858T PTPN22 PBMC treated with lipoplexes at the indicated dose for 72 hrs, with the same two set of primers as above described. Electropherograms show both C1858 and T1858 alleles in rtq-PCR products from untreated PBMC (RPMI) when using primers detecting whole target mRNA, while the sole T1858 SNP is shown when using variant specific set of primers. (C) Histogram shows the target mRNA detection of either set of primers in a single representative experiment. Primers used are indicated in the histogram legend.

To ascertain lipoplexes variant specificity, a second set of primers aimed to detect T1858 variant mRNA solely was designed. These primers were first validated by performing the rtq-PCR on PBMC derived from wild-type PTPN22 T1D patients using both set of primers, the new specific one and the first one able to recognize all target gene mRNA. The result of this validation showed the inability of the specific set to detect wild-type PTPN22 mRNA where the T1858 SNP is not present (FIG. 6, A). Subsequently, these primers were tested on the mRNA of heterozygous C1858T PTPN22 T1D PBMC treated as above described for 72 hrs. In this specific experiment, the new primers clearly revealed the presence of the variant mRNA and reported its decrease upon lipoplexes treatment (FIG. 6, B and C)

Lipo/siRNA SNP_T Lipoplexes Efficacy Toward Lyp Biological Activity

Figure 7:
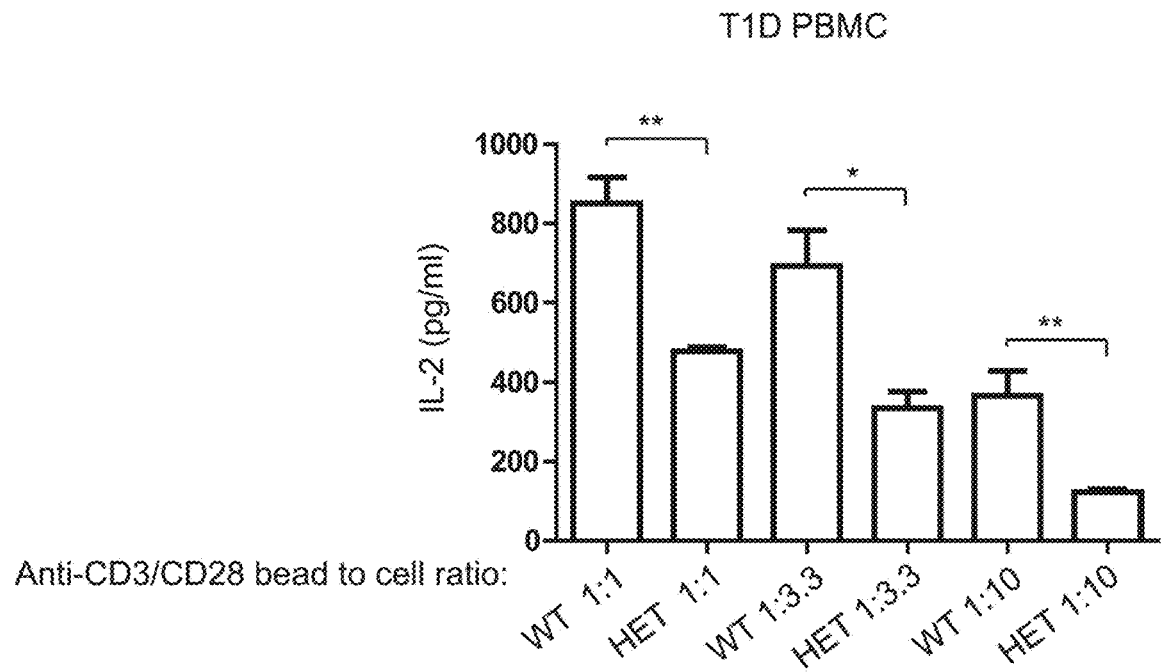
FIG. 7. Differential response to TCR stimulation in T1D PBMC. Histogram shows the divergent levels of IL-2 secretion in supernatants of T1D PBMC between HET C1858T PTPN22 and WT PTPN22 patients after activation with anti-CD3/CD28 beads with a bead to cell ratio of 1:1, 1:3,3, 1:10 for 20 hrs. The amount of IL-2 assayed by the specific ELISA test was normalized to the total protein load of each sample. For WT vs HET comparison ** indicates Unpaired t test P value=0.0014 for the 1:1 and P value=0.0086 for the 1:10 bead to cell ratio, * indicates Unpaired t test P value=0.0115 for the 1:3.3 bead to cell ratio.

Autoimmune disease associated R620W Lyp variant is a gain-of-function form of the enzyme (Vang 2005; Lin 2016), meaning that a more potent phosphatase activity of the protein is indeed present. Data from literature (Vang 2005) showing a decreased secretion of IL-2 by heterozygous C1858T PTPN22 PBMC in comparison to wild-type PTPN22 PBMC after stimulation with anti-CD3/CD28 beads were confirmed in T1D patients (FIG. 7). This significantly diverse response to TCR engagement was observed in all the activating conditions used (bead to cell ratios 1:1; 1:3,3; 1:10) (FIG. 7).

Figure 8:
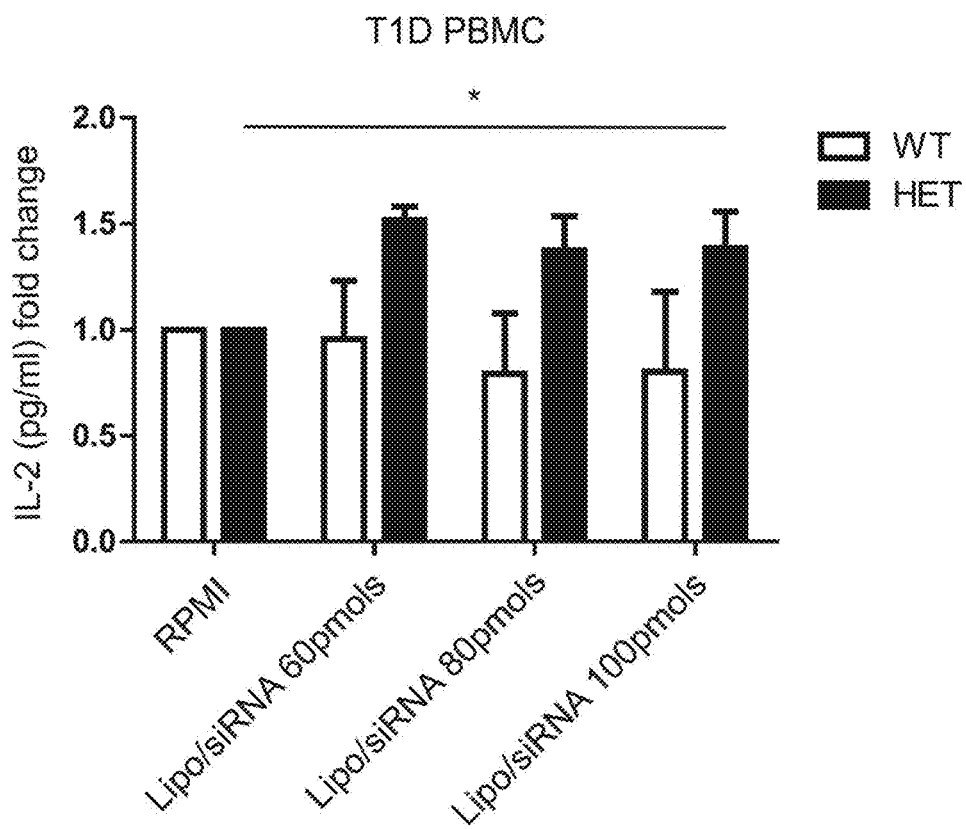
FIG. 8. IL-2 detection in culture supernatants of transfected then anti-CD3/CD28 stimulated PBMC. Histogram illustrates the increment of IL-2 secretion upon 20 hrs of anti-CD3/CD28 activation (bead to cell ratio 1:10) in culture supernatants of T1D C1858T PTPN22 HET PBMC that have been previously transfected O/N with lipoplexes at the indicated doses. The same significant increase in the IL-2 levels was not observed for the accordingly treated WT T1D PBMC. * indicates one-way analysis of variance P value=0.0491 for the HET PBMC. The amount of IL-2 was normalized to the total protein load of each sample (estimated by Pierce™ Thermo Scientific BCA (Rockford, IL) colorimetric protein assay kit).
Figure 9:
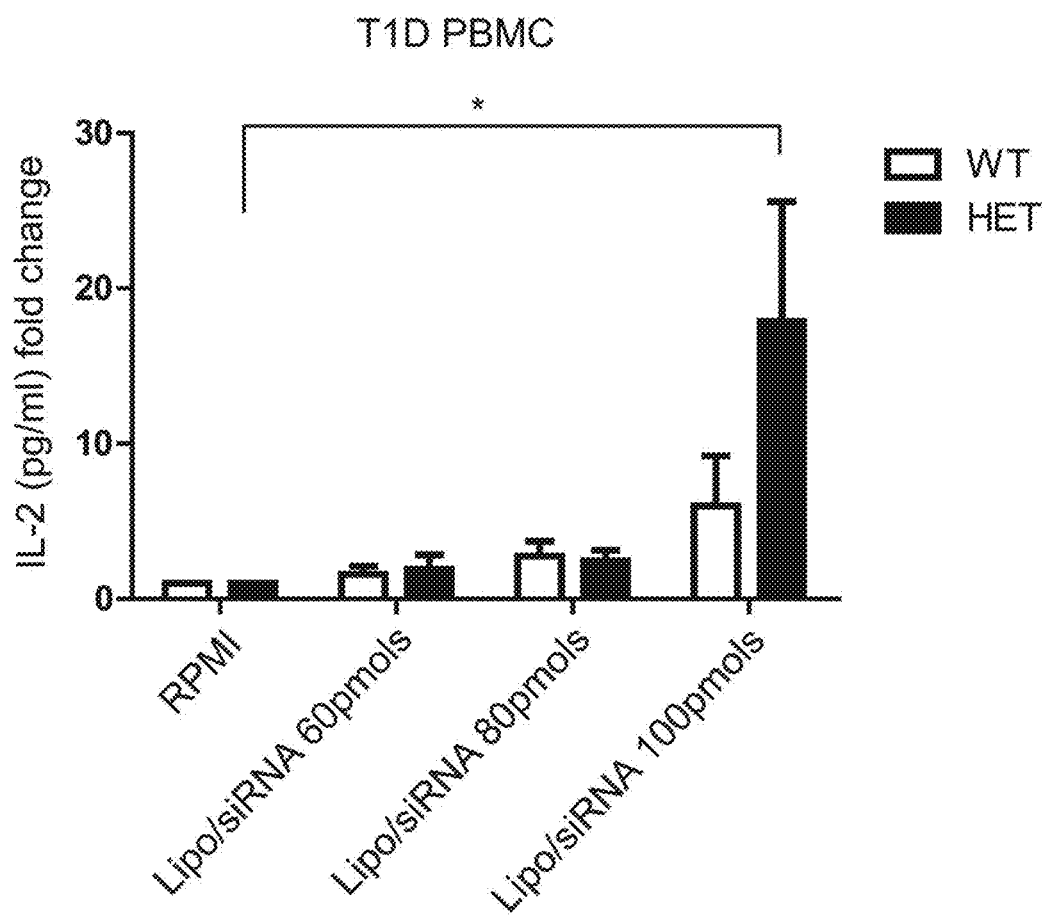
FIG. 9. IL-2 detection in PBMC cultures supernatants under suboptimal anti-CD3/CD28 stimulation. Histogram illustrates the increment of IL-2 secretion upon 5 days of anti-CD3/CD28 activation (bead to cell ratio 1:50) of HET C1858T PTPN22 T1D PBMC following O/N transfection with lipoplexes at the indicated doses. The same significant increase in the IL-2 levels was not observed for the accordingly treated WT T1D PBMC. * indicates one-way analysis of variance P value=0.0173 for the HET PBMC. The amount of IL-2 was normalized to the total protein load of each sample.

After TCR engagement, an increased concentration of IL-2 upon lipoplexes treatment in respect to untreated cells (RPMI) was observed in heterozygous C1858T PTPN22 T1D PBMC in comparison to wild-type PTPN22 T1D PBMC (FIG. 8). The same result was obtained and more evident using a suboptimal condition for stimulation with anti-CD3/CD28 beads (FIG. 9). This observation implies that the 'gain of function' effect of Lyp R620W on the TCR signaling pathway (Vang 2005) can be rescued following treatment with lipoplexes. As a final consequence, this mode of action could restore normal Lyp regulatory performance.

Evaluation of Lipo/siRNA for In Vivo Studies in Mice.

Figure 10:
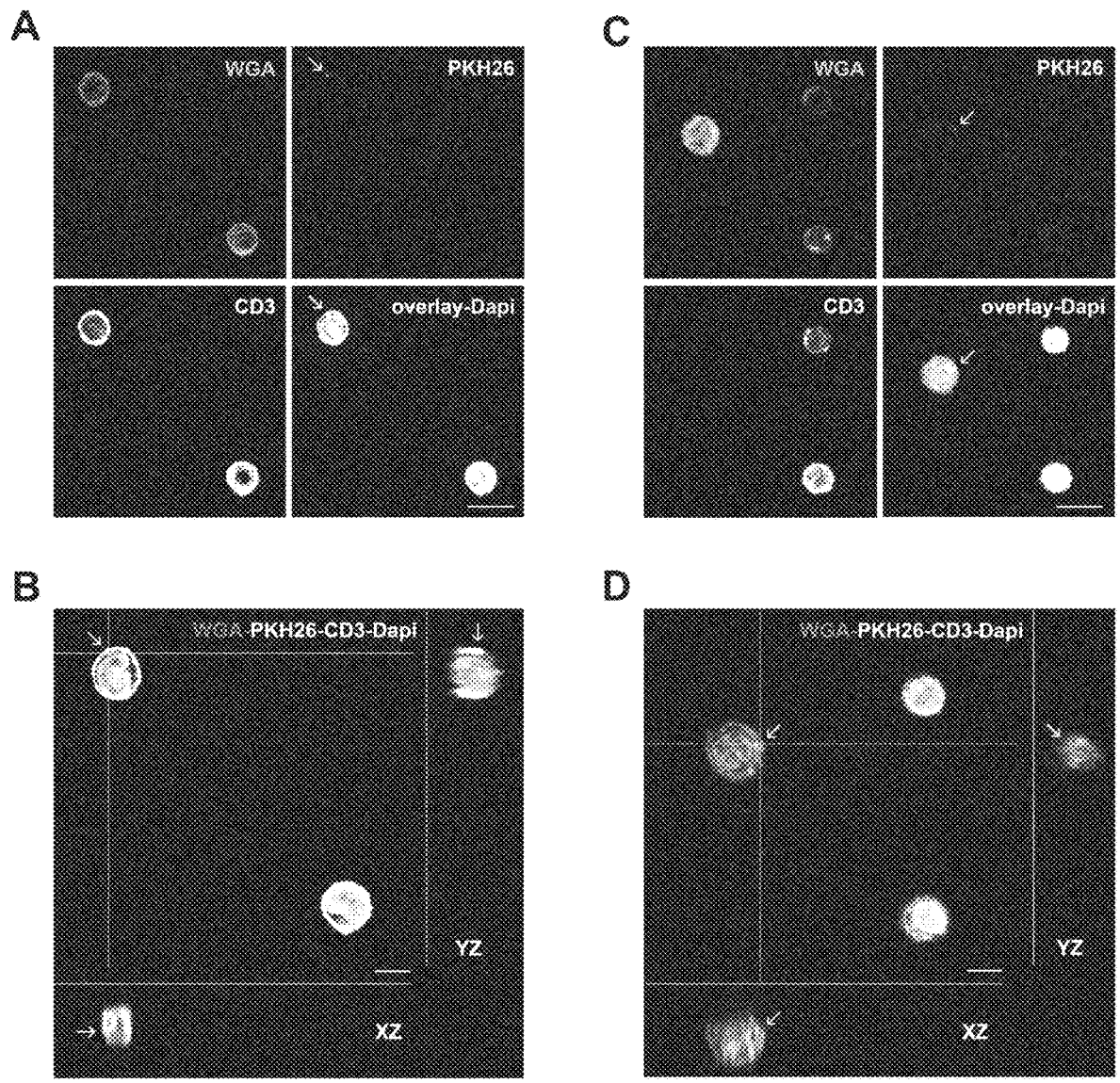
FIG. 10. Evaluation of PKH26-labelled Lipo/siRNA for in vivo mice studies. Confocal microscopy analysis of PKH26-labelled Lipo/siRNA internalization in human donor (HD) PBMC. Confocal microscopy analysis of Lipo/siRNA internalization in CD3 positive (A-B) and negative (C-D) cells. XY-Z orthogonal projections of confocal images (B, D) show the distribution of siRNA molecules close to/beneath the cell membrane in both CD3+ and CD3-lymphocytes (arrows).

Internalization of PKH26-labelled Lipo/siRNA complexes (100 pmols of siRNA) was visualized in HD PBMC following 4 and a half hrs of incubation (FIG. 10, A-D; arrows indicate lipoplexes positive to PKH26; WGA and DAPI indicate membrane and nuclei respectively. Analysis of X-and Y-axis projections of Z-reconstructions of confocal single optical sections (FIG. 10, B, D) allowed clear detection of lipoplexes beneath the cell membrane. The presence of PKH26 fluorescence inside cells further indicates the efficacy of this delivery system in the internalization of siRNA molecules inside HD PBMC, as previously observed for Jurkat T cells, healthy donor PBMC (Perri 2017) and T1D PBMC (vide supra, Pellegrino, 2018). The internalization was confirmed specifically in both CD3+ (white) and CD3-T lymphocytes (FIG. 10, A-D).

HD PBMC treated with PKH26-conjugated lipoplexes for 4 and a half hrs retained proper morphology both of the cell membrane (WGA stain) and of the nuclei (DAPI stain) as revealed by confocal microscopy (FIG. 10). These cell compartments did not show signs of damage or apoptosis respectively (FIG. 10).

In Flow-cytometry analysis, HD PBMC revealed high percentage of PKH26+ cells implying relevant transfection efficacy and internalization and, at the same time, showed low percentage of dead cells (PKH26+DAPI+ cells) (FIG. 11) as observed for rhodamine-marked lipoplexes (FIG. 3) indicative of low lipoplexes toxicity at this specific timing of the experimental procedure. Same results were obtained for monocytes within PBMC samples (FIG. 12).

Preliminar Evaluation of Biodistribution of Lipo/siRNA in representative mice.

After 24 hours from injection PKH26-labelled lipoplexes were not identified in the peripheral blood while these identified different percentages of cells within the organs under investigation (FIG. 13-15). Cells retained proper morphology both of the cell membrane (WGA stain) and of the nuclei (DAPI stain) as revealed also by confocal microscopy (FIG. 13-14). These cell compartments did not show signs of damage or apoptosis respectively (FIG. 13-14).

Preliminary Evaluation of Incorporation and Toxicity on Human PBMC of Lipoplexes Functionalized with PEG-Lipid-F9 (PEG-F9 Lipoplexes)

Preliminary experiments where conducted by confocal microscopy and Flow cytometry (data not shown) demonstrating that PEG-lipid-F9 lipoplexes marked with PKH26 are incorporated in PBMC after 4 and a half hrs of incubation and are not toxic to treated cells.

REFERENCES

Fierabracci A, Milillo A, Locatelli F, Fruci D. The putative role of endoplasmatic reticulum aminopeptidases in autoimmunity: insights from genome-wide association studies. Autoimmun Rev 2012; 12, 281-288.

Atkinson M A, Eisenbarth G S, Michels A W. Type 1 diabetes. *Lancet* 2014; 383:69-82. doi: 10.1016/S0140-6736 (13) 60591-7.

Mclachlan S M, Rapoport B. Breaking tolerance to thyroid antigens: changing concepts in thyroid autoimmunity. *Endocr Rev* 2014; 35:59-105. doi: 10.1210/er.2013-1055.

Hughes J W, Riddlesworth T D, DiMeglio L A, Miller K M, Rickels M R, McGill J B; T1D Exchange Clinic Network. Autoimmune Diseases in Children and Adults With Type 1 Diabetes From the T1D Exchange Clinic Registry. *J Clin Endocrinol Metab* 2016; 101:4931-37.

Harron K L, Mckinney P A, Feltbower R G, Bodansky H J, Norman P D, Campbell F M, et al. Incidence rate trends in childhood type 1 diabetes in Yorkshire, UK 1978-2007: effects of deprivation and age at diagnosis in the South Asian and non-South Asian populations. *Diabet Med* 2011; 28:1508-13. doi: 10.1111/j.1464-5491.2011.03413.x.

Woittiez N J, Roep B O. Impact of disease heterogeneity on treatment efficacy of immunotherapy in Type 1 diabetes: different shades of gray. *Immunotherapy* 2015; 7:163-74. doi: 10.2217/imt. 14.104.

Wiebolt J, Koeleman B P, van Haeften T W. Endocrine autoimmune disease: genetics become complex. *Eur J Clin Invest* 2010; 40:1144-55. doi: 10.1111/j.1365-2362.2010.02366.x.

Bottini N, Musumeci L, Alonso A, Rahmouni S, Nika K, Rostamkhani M, et al. A functional variant of lymphoid tyrosine phosphatase is associated with type I diabetes. *Nat Genet* 2004; 36:337-8.

Gianchecchi E, Palombi M, Fierabracci A. The putative role of the C1858T polymorphism of protein tyrosine phosphatase PTPN22 gene in autoimmunity. *Autoimmun Rev* 2013; 12:717-25

Perri V, Pellegrino M, Ceccacci F, Scipioni A, Petrini S, Gianchecchi E, et al. Use of short interfering RNA delivered by cationic liposomes to enable efficient down-regulation of PTPN22 gene in human T lymphocytes. *PLoS One* 2017;12: e0175784. doi: 10.1371/journal.pone.0175784.

Vandiedonck C, Capdevielle C, Giraud M, Krumeich S, Jais J P, Eymard B, et al. Association of the PTPN22*R620W polymorphism with autoimmune myasthenia gravis. *Ann Neurol* 2006; 59:404-7

Sadovnick A D. Genetic background of multiple sclerosis. *Autoimmun Rev* 2012; 11:163-6. doi: 10.1016/j.autrev.2011.05.007

Orozco G, Sánchez E, González-Gay M A, López-Nevot M A, Torres B, Cáliz R, et al. Association of a functional single-nucleotide polymorphism of PTPN22, encoding lymphoid protein phosphatase, with rheumatoid arthritis and systemic lupus erythematosus. *Arthritis Rheum* 2005; 52:219-24

Jagiello P, Aries P, Arning L, Wagenleiter S E, Csernok E, Hellmich B, et al. The PTPN22 620W allele is a risk factor for Wegener's granulomatosis. *Arthritis Rheum* 2005; 52:4039-43.

Hinks A, Barton A, John S, Bruce I, Hawkins C, Griffiths C E, et al. Association between the PTPN22 gene and rheumatoid arthritis and juvenile idiopathic arthritis in a UK population: further support that PTPN22 is an autoimmunity gene. *Arthritis Rheum* 2005; 52:1694-9

Lee H S, Korman B D, Le J M, Kastner D L, Remmers E F, Gregersen P K, et al. Genetic risk factors for rheumatoid arthritis differ in Caucasian and Korean populations. *Arthritis Rheum* 2009; 60:364-71. doi: 10.1002/art.24245.

Gourh P, Tan F K, Assassi S, Ahn C W, McNearney T A, Fischbach M, et al.

Association of the PTPN22 R620W polymorphism with anti-topoisomerase I- and anticentromere antibody-positive systemic sclerosis. *Arthritis Rheum* 2006; 54:3945-53.

Vang T, Congia M, Macis M D, Musumeci L, Orrú V, Zavattari P, et al. Autoimmune-associated lymphoid tyrosine phosphatase is a gain-of-function variant. *Nat Genet* 2005; 37:1317-9

Gianchecchi E, Crinò A, Giorda E, Luciano R, Perri V, Lorusso A, et al. Altered B cell homeostasis and toll-like receptor 9-driven response in type 1 diabetes carriers of the C1858T PTPN22 allelic variant: implications in the disease pathogenesis. *PLoS ONE* 2014; 9: e110755.

Metzler G, Dai X, Thouvenel C D, Khim S, Habib T, Buckner J H, et al. The Autoimmune Risk Variant PTPN22 C1858T Alters B Cell Tolerance at Discrete Checkpoints and Differentially Shapes the Naive Repertoire. *J Immunol* 2017; 199:2249-60. doi: 10.4049/jimmunol. 1700601.

Li M, Beauchemin H, Popovic N, Peterson A, d'Hennezel E, Piccirillo C A, et al. The common, autoimmunity-predisposing 620Arg>Trp variant of PTPN22 modulates macrophage function and morphology. *J Autoimmun* 2017; 79:74-83. doi: 10.1016/j.jaut.2017.01.009.

Maine C J, Hamilton-Williams E E, Cheung J, Stanford S M, Bottini N, Wicker L S, et al. PTPN22 alters the development of regulatory T cells in the thymus.

*J Immunol* 2012; 188:5267-75. doi: 10.4049/jimmunol. 1200150.

Wu D J, Zhou W, Enouz S, Orrú V, Stanford S M, Maine C J, et al. Autoimmunity associated LYP-W620 does not impair thymic negative selection of autoreactive T cells. *PLoS ONE* 2014; 9: e86677.

Zheng P, Kissler S. PTPN22 silencing in the NOD model indicates the type 1 diabetes-associated allele is not a loss-of-function variant. *Diabetes* 2013; 62:896-904.

Schölin A, Björklund L, Borg H, Arnqvist H, Björk E, Blohmé G, et al. Islet antibodies and remaining beta-cell function 8 years after diagnosis of diabetes in young adults: a prospective follow-up of the nationwide Diabetes Incidence Study in Sweden. *J Intern Med* 2004; 255:384-91.

Andersen M L, Rasmussen M A, Pörksen S, Svensson J, Vikre-Jørgensen J, Thomsen J, et al. Complex multi-block analysis identifies new immunologic and genetic disease progression patterns associated with the residual β-cell function 1 year after diagnosis of type 1 diabetes. *PLoS One* 2013; 8: e64632. doi: 10.1371/journal.pone.0064632.

Nielsen C, Hansen D, Husby S, Lillevang S T. Sex-specific association of the human PTPN22 1858T-allele with type 1 diabetes. *Int J Immunogenet* 2007; 34:469-73

Mainardi-Novo D T, Santos A S, Fukui R T, Gamberini M, Correia M R, Ruiz M O, et al. The PTPN22 1858T allele but not variants in the proximal promoter region of IL-21 gene is associated with the susceptibility to type 1 diabetes and the presence of autoantibodies in a Brazilian cohort. *Clin Exp Immunol* 2013; 172:16-22. doi: 10.1111/cei.12030

Petrone A, Suraci C, Capizzi M, Giaccari A, Bosi E, Tiberti C, et al. The protein tyrosine phosphatase nonreceptor 22 (PTPN22) is associated with high GAD antibody titer in latent autoimmune diabetes in adults: Non Insulin Requiring Autoimmune Diabetes (NIRAD) Study 3. *Diabetes Care* 2008; 31:534-8

Chelala C, Duchatelet S, Joffret M L, Bergholdt R, Dubois-Laforgue D, Ghandil P, et al. PTPN22 R620W functional variant in type 1 diabetes and autoimmunity related traits. *Diabetes* 2007; 56:522-6.

Maziarz M, Janer M, Roach J C, Hagopian W, Palmer J P, Deutsch K, et al. The association between the PTPN22 1858C>T variant and type 1 diabetes depends on HLA risk and GAD65 autoantibodies. *Genes Immun* 2010; 11:406-15. doi: 10.1038/gene.2010.12

Hermann R, Lipponen K, Kiviniemi M, Kakko T, Veijola R, Simell O, et al. Lymphoid tyrosine phosphatase (LYP/PTPN22) Arg620Trp variant regulates insulin autoimmunity and progression to type 1 diabetes. *Diabetologia* 2006; 49:1198-208.

Petrone A, Spoletini M, Zampetti S, Capizzi M, Zavarella S, Osborn J, et al. The PTPN22 1858T gene variant in type 1 diabetes is associated with reduced residual beta-cell function and worse metabolic control. *Diabetes Care* 2008; 31:1214-8. doi: 10.2337/dc07-1158.

Nielsen L B, Porksen S, Andersen M L, Fredheim S, Svensson J, Hougaard P, et al. The PTPN22 C1858T gene variant is associated with proinsulin in new-onset type 1 diabetes. *BMC Med Genet* 2011; 23; 12:41. doi: 10.1186/1471-2350-12-41.

Blasetti A, Di Giulio C, Tumini S, Provenzano M, Rapino D, Comegna L, et al. Role of the C1858T polymorphism of protein tyrosine phosphatase non-receptor type 22 (PTPN22) in children and adolescents with type 1 diabetes. *Pharmacogenomics J* 2017; 17:186-191. doi: 10.1038/tpj.2016.6.

Stanford S M, Krishnamurthy D, Falk M D, Messina R, Debnath B, Li S, et al. Discovery of a novel series of inhibitors of lymphoid tyrosine phosphatase with activity in human T cells. *J Med Chem* 2011; 54:1640-54. doi: 10.1021/jm101202j.

Vang T, Xie Y, Liu W H, Vidovic D, Liu Y, Wu S, et al. Inhibition of lymphoid tyrosine phosphatase by benzofuran salicylic acids. J Med Chem 2011; 54:562-71. doi: 10.1021/jm101004d.

He Y, Liu S, Menon A, Stanford S, Oppong E, Gunawan A M, et al. A potent and selective small-molecule inhibitor for the lymphoid-specific tyrosine phosphatase (LYP), a target associated with autoimmune diseases. *J Med Chem* 2013; 56:4990-5008. doi: 10.1021/jm400248c.

Opanasopit P, Paecharoenchai O, Rojanarata T, Ngawhirunpat T, Ruktanonchai U. Type and composition of surfactants mediating gene transfection of polyethylenimine-coated liposomes. *Int J Nanomedicine* 2011; 6:975-83.

Liu X. Targeting polo-like kinases: a promising therapeutic approach for cancer treatment. *Transl Oncol* 2015; 8:185-95.

Watts J K, Corey D R Gene silencing by siRNAs and antisense oligonucleotides in the laboratory and the clinic. *J Pathol* 2012; 226:365-79.

Dutta C, Avitahl-Curtis N, Pursell N, Larsson Cohen M, Holmes B, Diwanji R, et al. Inhibition of glycolate oxidase with dicer-substrate siRNA reduces calcium oxalate deposition in a mouse model of primary hyperoxaluria type 1. Mol Ther 2016; 24:770-8.

Joly F, Ray-Coquard I, Fabbro M, Donoghoe M, Boman K, Sugimoto A, et al. Decreased hypersensitivity reactions with carboplatin-pegylated liposomal doxorubicin compared to carboplatin-paclitaxel combination: analysis from the GCIG CALYPSO relapsing ovarian cancer trial. *Gynecol Oncol* 2011; 122:226-32.

Kudoh K, Takano M, Kouta H, Kikuchi R, Kita T, Miyamoto M, et al. Effects of bevacizumab and pegylated liposomal doxorubicin for the patients with recurrent or refractory ovarian cancers. *Gynecol Oncol* 2011; 122:233-37.

Petre C E, Dittmer D P. Liposomal daunorubicin as treatment for Kaposi's sarcoma. *Int J Nanomedicine* 2007; 2:277-88. PMID: 18019828

Andreakos E, Rauchhaus U, Stavropoulos A, Endert G, Wendisch V, Benahmed A S, et al. Amphoteric liposomes enable systemic antigen-presenting cell-directed delivery of CD40 antisense and are therapeutically effective in experimental arthritis. *Arthritis Rheum* 2009; 60:994-1005.

Bello C, Bombelli C, Borocci S, Di Profio P, Mancini G. Role of the spacer stereochemistry on the aggregation properties of cationic gemini surfactants. *Langmuir* 2006; 22:9333-8.

Bombelli C, Stringaro A, Borocci S, Bozzuto G, Colone M, Giansanti L, et al. Efficiency of liposomes in the delivery of a photosensitizer controlled by the stereochemistry of a gemini surfactant component. *Mol Pharm* 2010; 7:130-37.

Bombelli C, Faggioli F, Luciani P, Mancini G, Sacco M G. Efficient transfection of DNA by liposomes formulated with cationic gemini amphiphiles. *J Med Chem* 2005; 48:5378-82.

Bombelli C, Borocci S, Diociaiuti M, Faggioli F, Galantini L, Luciani P, et al. Role of the spacer of cationic gemini amphiphiles in the condensation of DNA. *Langmuir* 2005; 21:10271-4.

Seebach D, Kalinowski H O, Bastani B, Crass G, Daum H, Doerr H, et al. Preparation of auxiliaries for asymmetric synthesis from tartaric acid. Addition of butyllithium to aldehydes in chiral media. Helv Chim Acta 1977; 60:301-25.

Aleandri S, Bonicelli M G, Bordi F, Casciari S, Diociaiuti, Giansanti L, et al. How stereochemistry affects the physicochemical features of gemini surfactant based cationic liposomes. Soft Matter 2012; 8:5904-15.

Lin X, Pelletier S, Gingras S, Rigaud S, Maine C J, Marquardt K, et al. CRISPR-Cas9-mediated modification of the NOD mouse genome with Ptpn22R619W mutation increases autoimmune diabetes. *Diabetes* 2016; 65:2134-38.

Rillahan C D, Schwartz E, McBride R, Fokin V V, Paulson J C., Click and pick: identification of sialoside analogues for siglec-based cell targeting. Angew Chem Int Ed Engl. 2012 Oct. 29; 51 (44): 11014-8. doi: 10.1002/anie.201205831.

Büll C, Heise T, Adema G J, Boltje T J., Sialic Acid Mimetics to Target the Sialic Acid-Siglec Axis. Trends Biochem Sci. 2016 June; 41 (6): 519-531. doi: 10.1016/j.tibs.2016.03.007.

The invention claimed is:

1. A composition comprising a short interfering RNA duplex targeting PTPN22 C1858T single nucleotide polymorphism and a carrier, said short interfering RNA comprising the sequence 5'-AUGAUUCAGGUGUCCAUAC-3' (SEQ ID NO:2) and its complementary sequence 5'-GUAUGGACACCUGAAUCAU-3' (SEQ ID NO:1) and said carrier being functionalized with a monoclonal antibody against T lymphocytes, wherein the carrier is selected from the group consisting of a liposome, a nanocarrier and a PEGylated liposome.

2. The composition according to claim 1, wherein SEQ ID NO: 1 and 2 have a dinucleotide at 3' end, wherein said dinucleotide is chosen from the group consisting of dTdT, dAdA, dGdG and dCdC.

3. The composition according to claim 1, wherein said liposome is a cationic liposome comprising dimyristoyl-sn-glycero-phosphatidylcholine (DMPC) in combination with 2R,3S-2,3-dimethoxy-1,4-bis(N-hexadecyl-N,N-dimethylammonium)-butane dibromide, or in combination with 2S,3S-2,3-dimethoxy-1,4-bis(N-hexadecyl-N,N-dimethylammonium)-butane dibromide.

4. The composition according to claim 1, wherein said monoclonal antibody against T lymphocytes is the anti-CD3 monoclonal antibody teplizumab.

5. A pharmaceutical composition comprising the composition according to claim 1, in association with one or more excipients and/or adjuvants.

6. The composition according to claim 1, wherein said liposome is a cationic liposome.

7. The composition according to claim 1, wherein said nanocarrier is a solid-lipid nanoparticle.

8. The composition according to claim 1, wherein said carrier is a PEGylated liposome.

9. The composition according to claim 1, wherein said short interfering RNA consists of the sequence 5'-AUGAUUCAGGUGUCCAUAC-3' (SEQ ID NO:2) and its complementary sequence 5'-GUAUGGACACCUGAAUCAU-3' (SEQ ID NO:1).

10. The composition according to claim 1, wherein said liposome is a cationic liposome consisting of dimyristoyl-sn-glycero-phosphatidylcholine (DMPC) in combination with 2R,3S-2,3-dimethoxy-1,4-bis(N-hexadecyl-N,N-dimethylammonium)-butane dibromide.

11. The composition according to claim 1, wherein said liposome is a cationic liposome consisting of dimyristoyl-sn-glycero-phosphatidylcholine (DMPC) in combination with 2S,3S-2,3-dimethoxy-1,4-bis(N-hexadecyl-N,N-dimethylammonium)-butane dibromide.

\* \* \* \* \*

UNITED STATES PATENT AND TRADEMARK OFFICE
CERTIFICATE OF CORRECTION

PATENT NO. : 12,410,431 B2
APPLICATION NO. : 17/053816
DATED : September 9, 2025
INVENTOR(S) : Alessandra Fierabracci Page 1 of 1

It is certified that error appears in the above-identified patent and that said Letters Patent is hereby corrected as shown below:

On the Title Page

Item (30) Foreign Application Priority Data:
"(CN)" should be changed to --(IT)--

Signed and Sealed this
Thirteenth Day of January, 2026

John A. Squires
*Director of the United States Patent and Trademark Office*